United States Patent [19]

Takasu et al.

[11] 4,446,217
[45] May 1, 1984

[54] ELECTROPHOTOGRAPHIC PHOTOSENSITIVE MEMBER HAVING A HYDRAZONE CONTAINING LAYER

[75] Inventors: Yoshio Takasu, Tama; Shozo Ishikawa, Sayama, both of Japan

[73] Assignees: Canon Kabushiki Kaisha; Copyer Kabushiki Kaisha, both of Tokyo, Japan

[21] Appl. No.: 343,187

[22] Filed: Jan. 27, 1982

[30] Foreign Application Priority Data

Feb. 3, 1981 [JP] Japan .................................. 56-14515
Mar. 19, 1981 [JP] Japan .................................. 56-40145
May 20, 1981 [JP] Japan .................................. 56-75973

[51] Int. Cl.³ .................................................. G03G 5/06
[52] U.S. Cl. ........................................ 430/58; 430/60; 430/79; 430/96
[58] Field of Search ................... 430/82, 70, 75, 79, 430/58, 73, 59, 60, 96

[56] References Cited

U.S. PATENT DOCUMENTS

| | | | |
|---|---|---|---|
| 3,180,729 | 4/1965 | Klupfel et al. .................. | 96/1 |
| 3,378,554 | 4/1968 | Puschel et al. . | |
| 3,484,237 | 12/1969 | Shattuch et al. .................. | 96/1.5 |
| 3,684,502 | 8/1972 | Gramza et al. . | |
| 3,775,105 | 11/1973 | Kukla . | |
| 3,824,099 | 7/1974 | Champ et al. .................. | 96/1.5 |
| 3,837,851 | 9/1974 | Shattuch et al. .................. | 96/1.5 |
| 3,870,516 | 3/1975 | Smith et al. . | |
| 3,871,882 | 3/1975 | Wiedemann .................. | 96/1.5 |
| 3,877,935 | 4/1975 | Regensburger et al. ........... | 96/1.5 |
| 3,884,691 | 5/1975 | Rochlitz . | |
| 3,894,868 | 7/1975 | Regenshburger et al. . | |
| 4,150,987 | 4/1979 | Anderson et al. .................. | 96/1.5 |
| 4,251,614 | 2/1981 | Sasaki et al. .................. | 430/58 |
| 4,256,821 | 3/1981 | Enomoto et al. .................. | 430/59 |
| 4,260,672 | 4/1981 | Sasaki et al. .................. | 430/72 |
| 4,265,991 | 5/1981 | Hirai et al. .................. | 430/64 |
| 4,272,598 | 6/1981 | Sasaki et al. .................. | 430/72 |
| 4,278,747 | 7/1981 | Murayama et al. .................. | 430/82 |
| 4,279,981 | 7/1981 | Ohta et al. . | |
| 4,297,426 | 10/1981 | Sakai et al. . | |
| 4,338,388 | 7/1982 | Sakai et al. .................. | 430/79 |
| 4,365,014 | 12/1982 | Sakai et al. .................. | 430/79 |
| 4,367,273 | 1/1983 | Murayama et al. .................. | 430/79 |

FOREIGN PATENT DOCUMENTS

| | | |
|---|---|---|
| 2302522 | 8/1981 | Fed. Rep. of Germany . |
| 1030024 | 8/1963 | Italy . |
| 43-1619768 | 7/1968 | Japan . |
| 48-71236 | 9/1973 | Japan . |
| 51-94829 | 8/1976 | Japan . |
| 54-112637 | 9/1979 | Japan . |
| 54-119925 | 9/1979 | Japan . |
| 54-121742 | 9/1979 | Japan . |
| 55-17105 | 2/1980 | Japan . |
| 55-180667 | 8/1980 | Japan . |
| 930988 | 7/1968 | United Kingdom . |
| 1296390 | 11/1972 | United Kingdom . |
| 1453024 | 10/1976 | United Kingdom . |
| 1370197 | 10/1976 | United Kingdom . |
| 1465141 | 2/1977 | United Kingdom . |
| 1465142 | 2/1977 | United Kingdom . |
| 2001769A | 2/1979 | United Kingdom . |
| 2018446A | 10/1979 | United Kingdom . |
| 2034493A | 6/1980 | United Kingdom . |
| 2052082A | 1/1981 | United Kingdom . |
| 2055803A | 3/1981 | United Kingdom . |
| 2034494A | 6/1982 | United Kingdom . |

*Primary Examiner*—John E. Kittle
*Assistant Examiner*—John L. Goodrow
*Attorney, Agent, or Firm*—Fitzpatrick, Cella, Harper & Scinto

[57] ABSTRACT

An electrophotographic photosensitive member comprises a layer containing a hydrazone compound represented by the following formula (1) or (2):

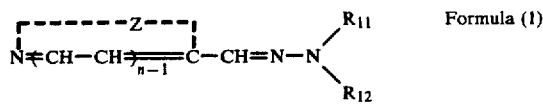

Formula (1)

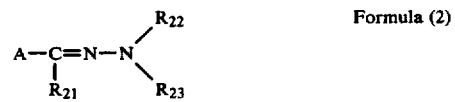

Formula (2)

wherein, Z is an atomic group necessary to complete a substituted or unsubstituted heterocyclic ring; $R_{11}$, $R_{12}$, $R_{21}$, $R_{22}$ and $R_{23}$ represent substituted or unsubstituted alkyl, substituted or unsubstituted aralkyl, or substituted or unsubstituted aryl, and the combinations of $R_{11}$ with $R_{12}$ and of $R_{22}$ with $R_{23}$ can form each a pyrrolidine ring, piperidine ring, or morpholine ring; n is 1 or 2; and A is a monovalent heterocyclic compound residue.

27 Claims, 1 Drawing Figure

ELECTROPHOTOGRAPHIC PHOTOSENSITIVE MEMBER HAVING A HYDRAZONE CONTAINING LAYER

BACKGROUND OF THE INVENTION

1. Field of the Invention

This invention relates to electrophotographic photosensitive members and more particularly to a photosensitive member having improved electrophotographic characteristics.

2. Description of the Prior Art

There have so far been known selenium, cadmium sulfide, zinc oxide, etc. as photoconductive materials for use in electrophotographic photosensitive members. In contrast to many advantages thereof, such as, for instance, chargeability in a dark to a suitable potential, a little dissipation of charge in a dark, and fast dissipation ability by light irradiation, these photoconductive materials have the disadvantages of lacking the film forming property per se with a very few exceptions such as amorphous selenium and of poor ability to retain the charge given to their surface.

On the other hand, a variety of organic photoconductive materials are known, including photoconductive polymers such as polyvinylcarbazole, polyvinylanthracene, N-acrylamidemethylcarbazole polymer (Japanese Patent Application Laid-Open No. 85337/1975), 6-vinylindols (2,3-6)quinoxaline polymer (Japanese Patent Application Laid-Open No. 93432/1950) and also photoconductive polymers sensitized with trinitrofluorenone (U.S. Pat. No. 3,484,237) or with 2-aza-9-fluorenone (Japanese Patent Application Laid-Open No. 71236/1973), which, however, cannot be said so useful in practice since they generally have neither enough sensitivity for actual uses nor a sufficient good film forming property. There are also known low-molecular organic photoconductors such as pyrazoline compounds disclosed in British Pat. No. 1030024 and U.S. Pat. No. 3,180,729 and styryl compounds disclosed in Japanese Patent Application Laid-Open No. 94828/1976 and British Pat. Nos. 1465141 and 1465142. These low-molecular organic photoconductors have solved the problem of film forming property, which has been an objection to the application of the above organic photoconductive polymers, by selection of a suitable binder, but involve still many difficulties in practical applications because of low sensitivity of most of these organic photoconductor.

In view of the above, a photosensitive member of laminate structure has been recently proposed which comprises two photosensitive layers, a charge generation layer and a charge transport layer, having allotted functions. The electrophotographic photosensitive member having such photosensitive layers of laminate structure has been improved in sensitivity to visible light, in charge retentivity, and in surface strength.

Such a photosensitive member is provided with a laminate structure of photosensitive layers such as, for example, the following upon its conductive layer:

(1) a charge generation layer containing a methine dye derived from squaric acid or Diane Blue and a charge transport layer containing a pyrazoline compound (U.S. Pat. Nos. 3,824,099 and 3,837,851 and British Pat. No. 1453024);

(2) a charge generation layer comprising a vacuum-deposited polycyclic quinone pigment and a charge transport layer containing a polyarylalkane compound (German Patent Offen. No. 2929518);

(3) a charge generation layer comprising a vacuum-deposited a perylene pigment and a charge transport layer containing 2,5-bis(4-diethylaminophenyl)-1,3,4-oxadiazole (U.S. Pat. No. 3,871,882);

(4) a charge generation layer containing a disazo pigment and a charge transport layer containing a spiropyrazoline compound (Japanese Patent Application Laid-Open No. 112637/1979), N-(4-dialkylaminophenyl)carbazole (Japanese Patent Application Laid-Open No. 119925/1979), or a diarylmethane compound (Japanese Patent Application Laid-Open No. 108667/1980);

(5) a charge generation layer containing a cyanine dye and a charge transport layer containing 1,3,4-oxadiazole derivative (Japanese Patent Application Laid-Open No. 121742/1979); and (6) a charge generation layer containing a methine dye derived from squaric acid or a disazo pigment and a charge transport layer containing a hydrazone compound (U.S. Pat. Nos. 4,150,987, and 4,278,747).

However, electrophotographic photosensitive members employing these compounds in the charge transport layer still do not have sufficient sensitivity and result in variations in surface potential particularly an increase in light portion potential and a decrease in dark portion potential, upon repeating charge and exposure. Additionally, these photosensitive members gain small quantities of charge at the surface upon corona charging and inferior in photomemory property.

SUMMARY OF THE INVENTION

An object of this invention is to provide novel electrophotographic photosensitive members of high sensitivity which are free from the above-mentioned disadvantages.

A further object of this invention is to provide electrophotograhic photosensitive members which result in minimum variations in light and dark portion potentials upon repeating operations of charging and exposure.

Another object of this invention is to provide electrophotographic photosensitive members exhibiting a high initial potential and a good photomemory property.

A still further object of this invention is to provide novel organic photoconductive materials or novel charge transporting substances.

According to the present invention, there is provided an electrophotographic photosensitive member comprising a layer containing a hydrazone compound represented by the following formula (1) or (2):

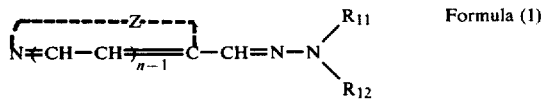

Formula (1)

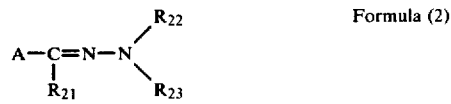

Formula (2)

wherein, Z is an atomic group necessary to complete a substituted or unsubstituted heterocyclic ring; $R_{11}$, $R_{12}$, $R_{21}$, $R_{22}$ and $R_{23}$ represent substituted or unsubstituted alkyl, substituted or unsubstituted aralkyl, or substituted or unsubstituted aryl, and the combinations of $R_{11}$ with $R_{12}$ and of $R_{22}$ with $R_{23}$ can form each a pyrrolidine ring, piperidine ring, or morpholine ring; n is 1 or 2, and A is a monovalent heterocyclic compound residue.

DESCRIPTION OF THE PREFERRED EMBODIMENTS

Figure 1:
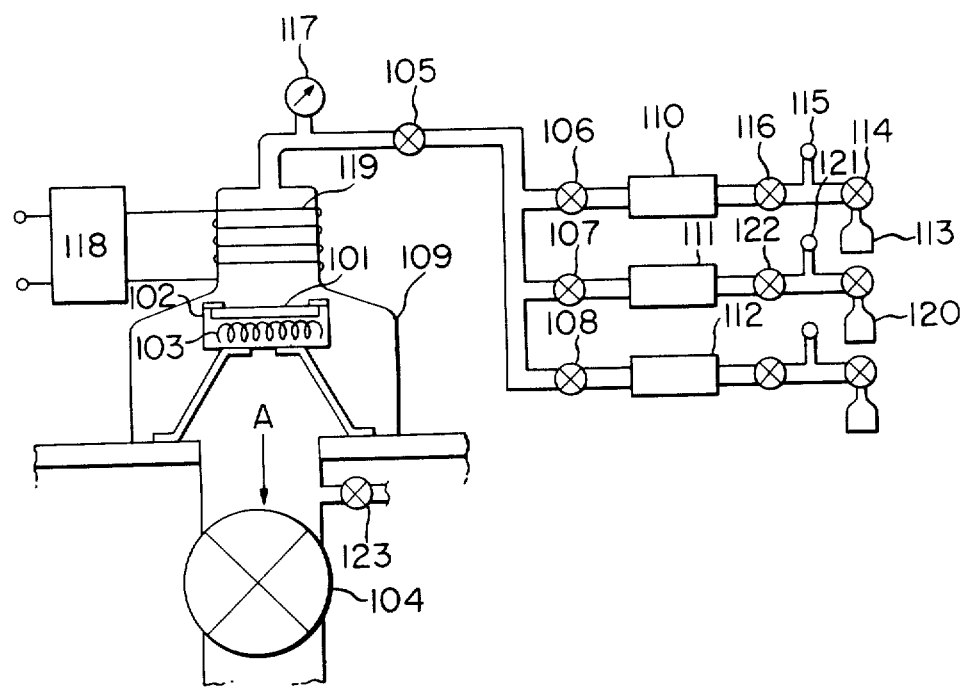
FIG. 1 is a schematic illustration of a device for forming a charge generation layer used in Examples 22, 45 and 58.

The photoconductive materials to be used in this invention are represented by formula (1) or (2).

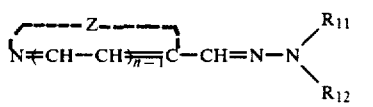

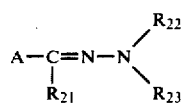

Z is an atomic group necessary to complete a heterocyclic ring such as thiazoline, oxazoline, imidazoline, thiazole, oxazole, imidazole, benzothiazole, benzoxazole, benzimidazole, naphthothiazole, naphthoxazole, naphthimidazole, quinolone (e.g., 2-quinoline or 4-quinoline), isoquinoline, quinoxaline, pyridazine, pyrimidine, pyrazine, triazole, oxadiazole or thiadiazole ring; and n is 1 or 2. These heterocyclic rings may also have substituents such as halogen atoms (e.g., chlorine, bromine and fluorine), alkyls (e.g., methyl, ethyl, n-propyl, isopropyl, n-butyl, sec-butyl, t-butyl, t-octyl, octyl, octadecyl, etc.), alkoxys (e.g., methoxy, ethoxy, butoxy, etc.), aryls (e.g., phenyl, tolyl, xylyl, etc.), aryloxys (e.g., phenoxy, methylphenoxy, chlorophenoxy, dimethylphenoxy, etc.), N-substituted aminos (e.g., N-methylamino, N-ethylamino, N-t-butylamino, N-octylamino, N-benzylamino, acetylamino, benzoylamino, etc.), N,N-disubstituted dimethylaminos (e.g., N,N-dimethylamino, N,N-diethylamino, N,N-dipropylamino, N,N-di-t-butylamino, N,N-dibenzylamino, N-ethyl-N-benzylamino, etc.), acyls (e.g., acetyl, propionyl, benzoyl, methylbenzoyl, dimethylbenzoyl, chlorobenzoyl, etc.), carbamoyl, sulfamoyl, etc.

$R_{11}$, $R_{12}$, $R_{21}$, $R_{22}$ and $R_{23}$ represent substituted or unsubstituted alkyl (e.g., methyl, ethyl, n-propyl, isopropyl, n-butyl, sec-butyl, t-butyl, n-amyl, t-amyl, hexyl, cyclohexyl, octyl, t-octyl, octadecyl, 2-hydroxyethyl, 3-hydroxypropyl, 2-chloroethyl, 3-chloropropyl, allyl, 2-methoxyethyl, 2-ethoxyethyl, 3-methoxypropyl, 3-ethoxypropyl, etc.), substituted or unsubstituted aralkyl (e.g., benzyl, phenetyl, methylbenzyl, dimethylbenzyl, chlorobenzyl, dichlorobenzyl, bromobenzyl, dibromobenzyl, methoxybenzyl, ethoxybenzyl, etc.), or substituted or unsubstituted aryl (e.g., phenyl, α-naphthyl, β-naphthyl, tolyl, xylyl, biphenyl, methoxyphenyl, ethoxyphenyl, chlorophenyl, dichlorophenyl, bromophenyl, dibromophenyl, etc.), wherein at least one of $R_{11}$ and $R_{12}$ or at least one of $R_{21}$ and $R_{22}$ are preferably said aryls. In addition, the combinations of $R_{11}$ with $R_{12}$ or of $R_{21}$ with $R_{22}$ can form each a pyrrolidine ring, piperidine ring, or morpholine ring.

A is a monovalent heterocyclic residue of compounds such as, for example, pyrrole, pyrazole, pyrimidine, pyridazine, pyridine, indole, benzimidazole, carbazole, furan, oxazole, benzoxazole, benzofuran, dibenzofuran, thiophene, thiazole, benzothiazole, and the like. These heterocyclic compounds may also have substituents such as for example, halogen atoms (e.g., fluorine, chlorine, and bromine), nitro, alkoxys (e.g., methoxy, ethoxy, butoxy, etc.), substituted or unsubstituted alkyls (e.g., methyl, ethyl, n-propyl, n-butyl, t-butyl, n-octyl, t-octyl, benzyl, methylbenzyl, allyl, etc.), aryloxys (e.g., phenoxy, methylphenoxy, chlorophenoxy, acetylphenoxy, etc.), acyls (e.g., acetyl, propionyl, benzoyl, methylbenzoyl, etc.), and substituted or unsubstituted aminos (e.g., amino, N,N-dimethylamino, N,N-diethylamino, N,N-dipropylamino, acetylamino, benzoylamino, etc.).

Individual examples of the hydrazone compounds represented by formula (1) are enumerated below.

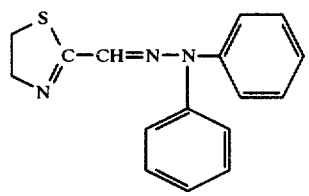

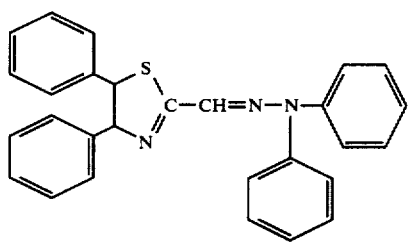

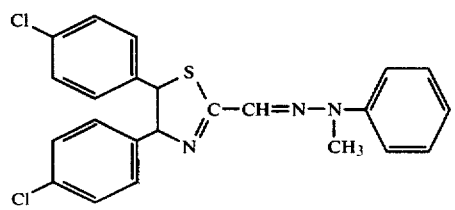

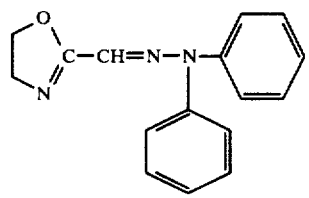

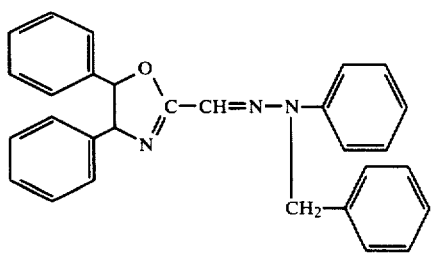

-continued (6) — (19): chemical structures

-continued

(20) [structure]

(21) [structure]

(22) [structure]

(23) [structure]

(24) [structure]

(25) [structure]

(26) [structure]

-continued

(27) [structure]

(28) [structure]

(29) [structure]

(30) [structure]

(31) [structure]

(32) [structure]

(33) [structure]

-continued
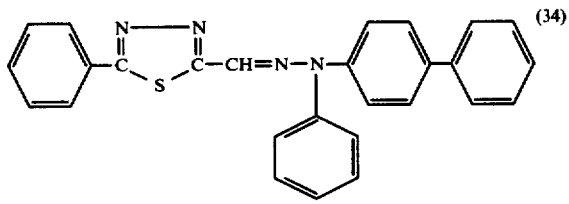 (34)
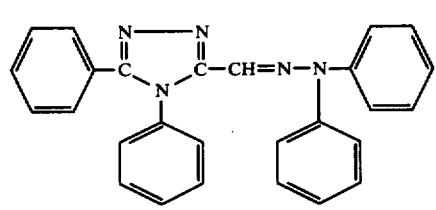 (35)
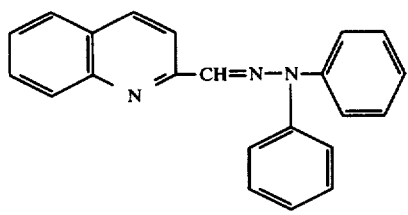 (36)
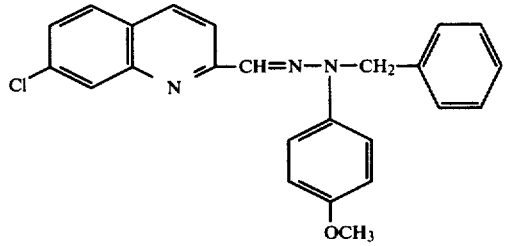 (37)
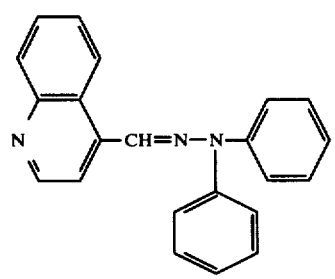 (38)
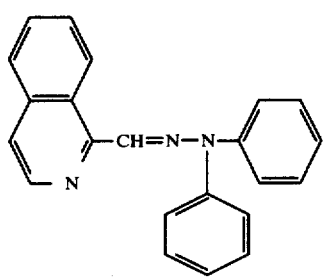 (39)
-continued
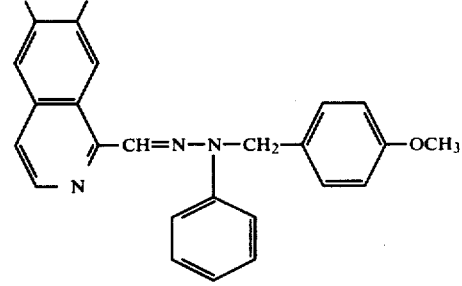 (40)
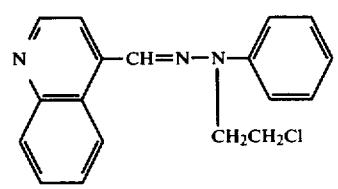 (41)
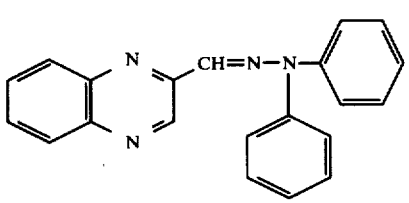 (42)
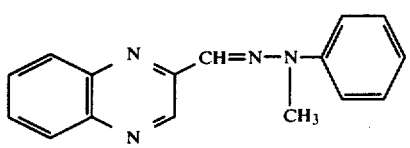 (43)
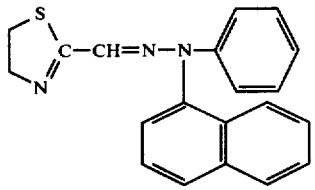 (44)
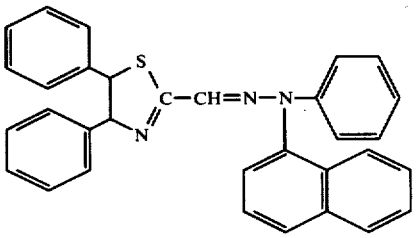 (45)
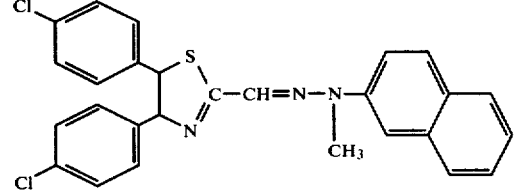 (46)

-continued
 (47)
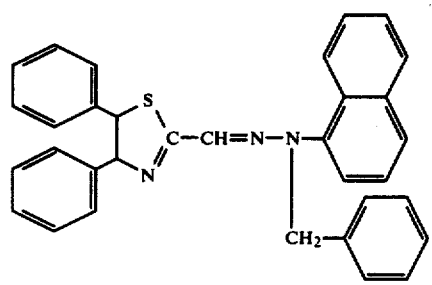 (48)
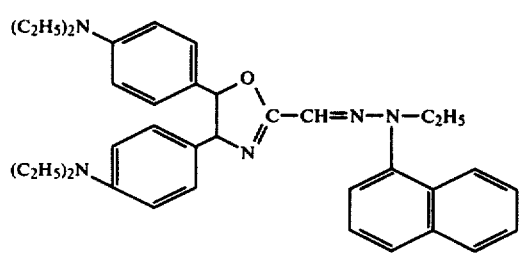 (49)
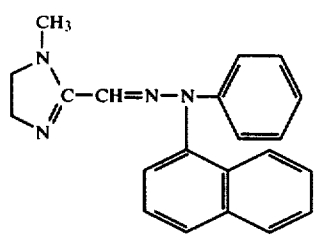 (50)
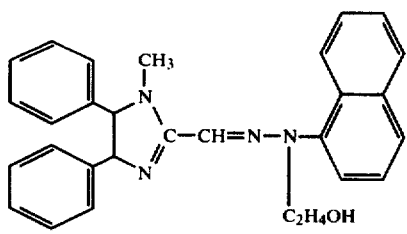 (51)
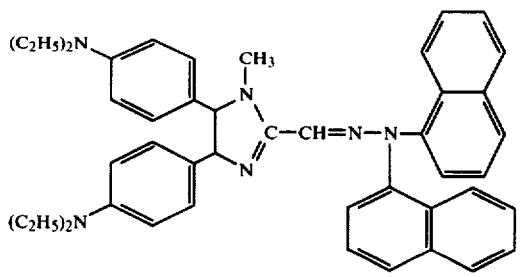 (52)
-continued
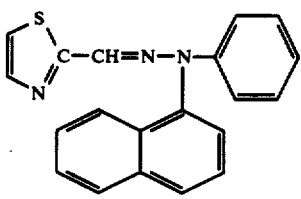 (53)
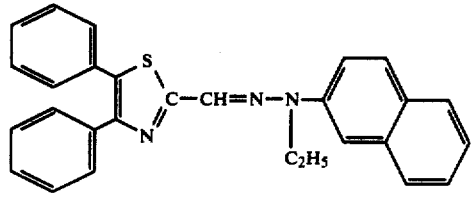 (54)
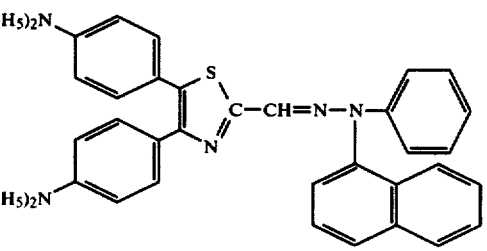 (55)
 (56)
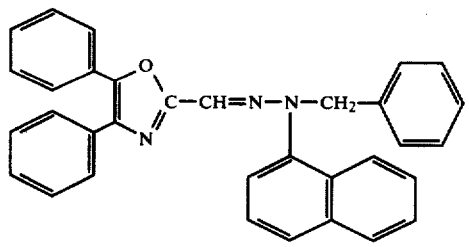 (57)
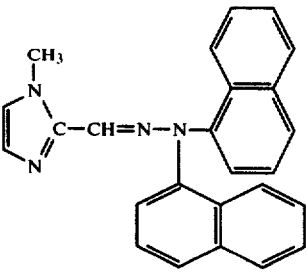 (58)

-continued
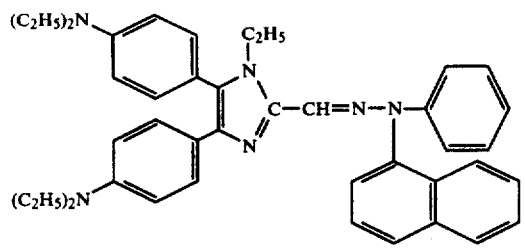 (59)
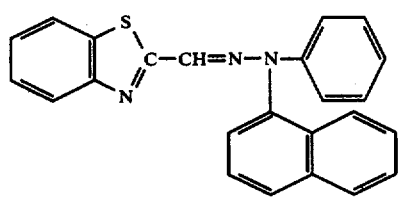 (60)
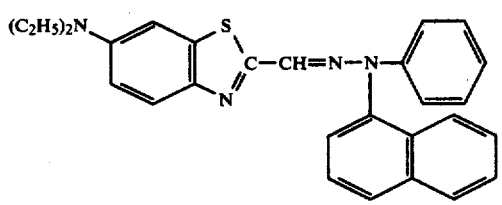 (61)
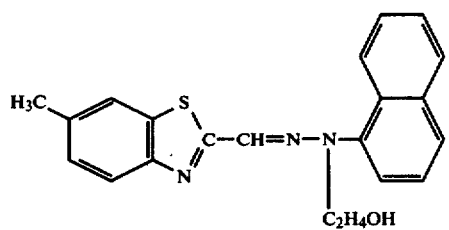 (62)
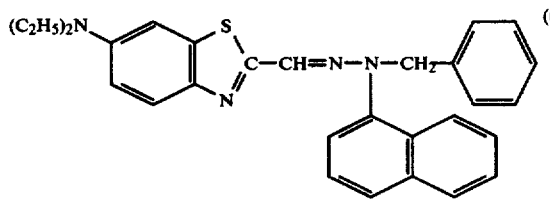 (63)
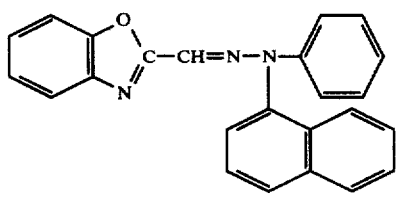 (64)
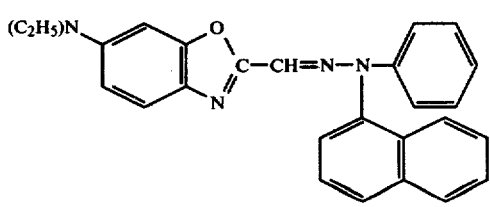 (65)
-continued
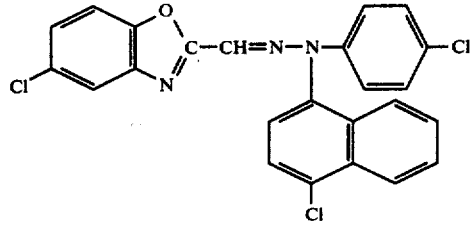 (66)
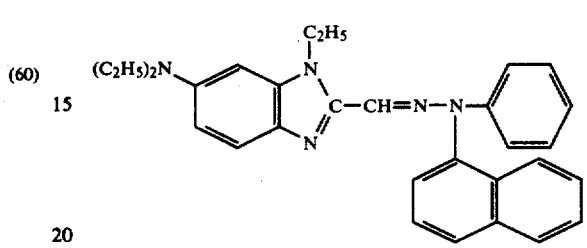 (67)
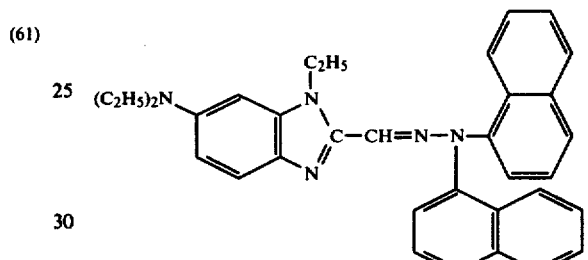 (68)
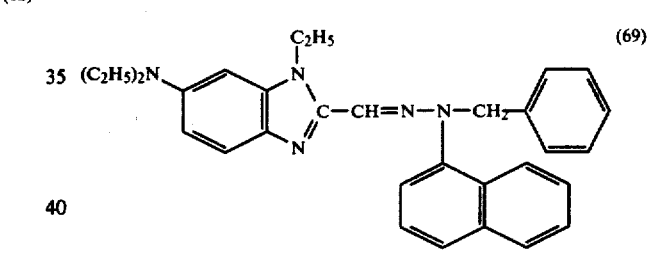 (69)
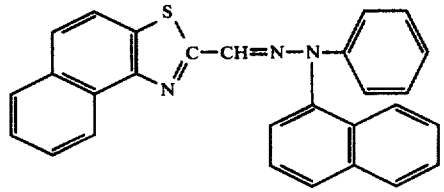 (70)
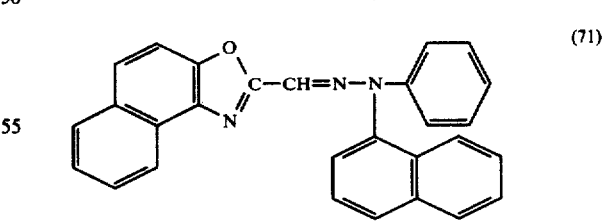 (71)
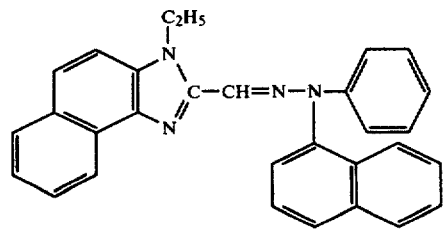 (72)

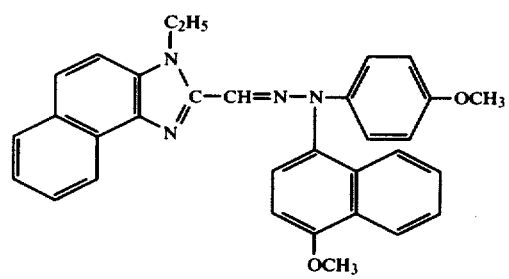
(73)
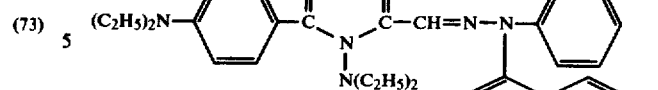
(80)
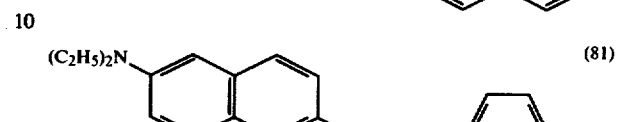
(74)
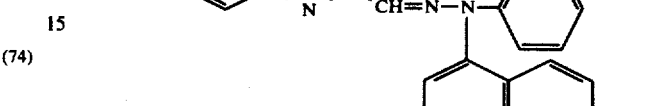
(81)
(75)
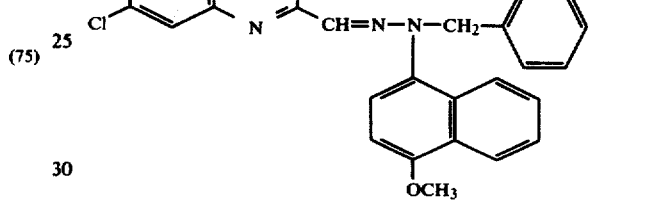
(82)
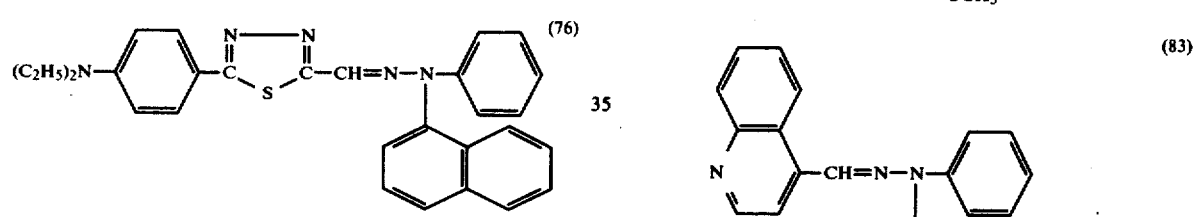
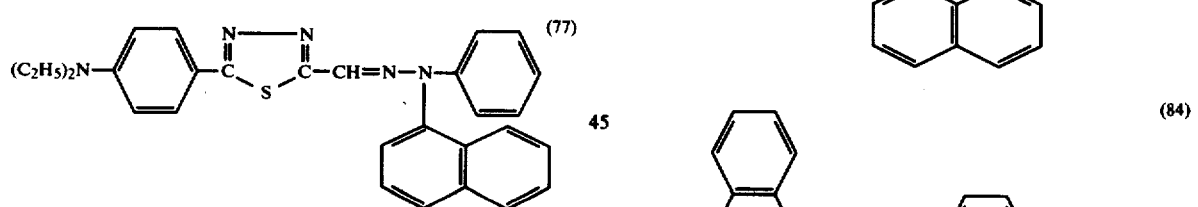
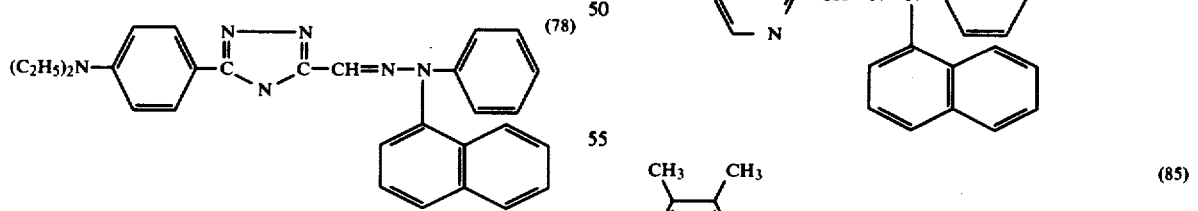
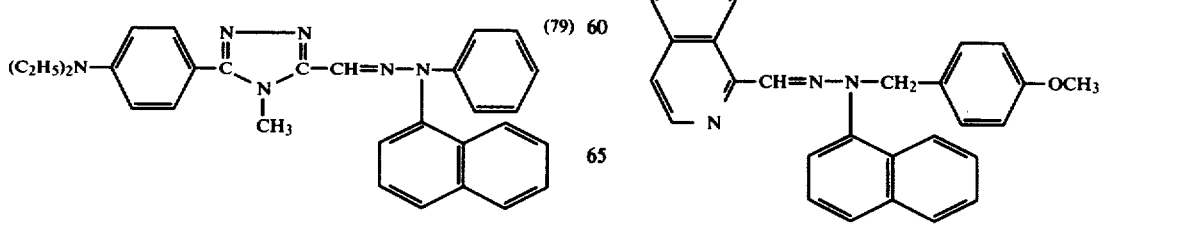

Typical examples of the hydrazone compounds represented by formula (2) are as follows:

-continued

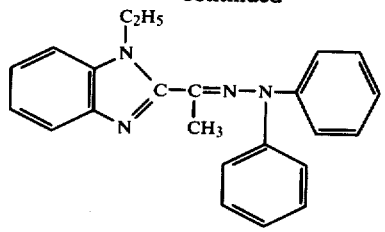

(101)

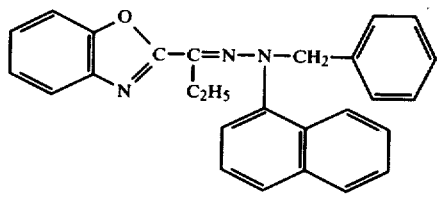

(102)

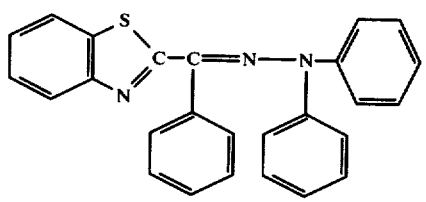

(103)

The above-cited compounds can be readily synthesized in known ways. For instance, hydrazone compounds represented by formula (1) can be obtained by the condensation of hydrazines represented by the following formula (A) or their inorganic salts with aldehydes represented by the following formula (B) in a solvent according to the usual method:

Formula (A)

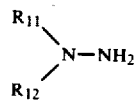

Formula (B)

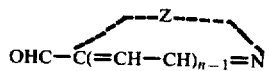

wherein $R_{11}$, $R_{12}$, Z and n are the same as in formula (1). The solvents applicable to this reaction are methanol, ethanol, tetrahydrofuran, etc.

Hydrazone compounds represented by formula (2) can be readily obtained, for instance, by the condensation of ketones represented by the following formula (C) and hydrazines represented by the following formula (D) in a suitable solvent (e.g., methanol, ethanol, 1,4-dioxane, tetrahydrofuran, methyl Cellosolve, ethyl Cellosolve, dimethylformamide, acetic acid, etc.):

Formula (C)

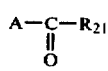

Formula (D)

-continued

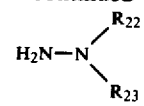

wherein A, $R_{21}$, $R_{22}$ and $R_{23}$ are the same as in formula (2).

The process for synthesizing typical hydrazone compounds used in this invention will be illustrated by the following examples:

SYNTHESIS EXAMPLE 1 (SYNTHESIS OF HYDRAZONE COMPOUND NO. 2)

In 5 liter of 35% hydrochloric acid was dissolved 193 g (1.14 mol) of diphenylamine, of which nitroso derivative was formed by adding 87 g (1.26 mol) of sodium nitrite. After the reaction mixture was cooled to 10° C., 87.5 g (1.14 mol) of zinc dust in limited amounts was added. The resulting mixture was then filtered and water was poured into the filtrate to isolate a hydrazine compound, 1,1-diphenylhydrazine. The hydrazine thus obtained was dissolved in a mixture of 1 l of ethanol and 50 ml of acetic acid, and 304 g (1.14 mol) of 2-formyl-4,5-diphenylthiazoline, which is represented by the formula

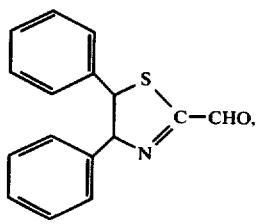

was added. The resulting mixture was cooled to 10° C., and 250 g (3.82 mol) of zinc metal was added with caution not to raise a temperature over 20° C. The reaction mixture was filtered, and the filtrate was poured into water, thus giving a yellow precipitate. The precipitate was recrystallized three times from methyl ethyl ketone, and 104.6 g of yellow crystals were obtained (yield on the amine: 21.2%).

| | Elementary analysis: | |
|---|---|---|
| | Calcd. for $C_{28}H_{23}N_3S$ (%) | Found (%) |
| C | 77.60 | 77.57 |
| H | 5.31 | 5.33 |
| N | 9.70 | 9.68 |

SYNTHESIS EXAMPLE 2 (SYNTHESIS OF HYDRAZONE COMPOUND NO. 5)

1-benzyl-1-phenylhydrazine was prepared in the same manner as Synthesis Example 1 except for using 208.6 g (1.14 mol) of N-benzylaniline in place of diphenylamine. Said hydrazine was dissolved in a mixture of 1 l of ethanol and 50 ml of acetic acid, and 286 g (1.14 mol) of 2-formyl-4,5-diphenyloxazoline, represented by the formula

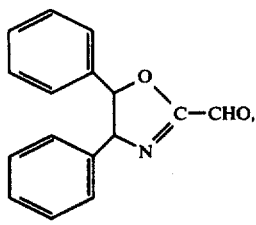

was added. The resulting mixture was cooled to 10° C., and 250 g (3.82 mol) of zinc metal was added with caution not to raise the temperature over 20° C. After completion of the reaction, the reaction mixture was filtered and the filtrate was poured into water, thus giving a yellow precipitate. Recrystallization of the precipitate from a methyl ethyl ketone-ethanol (1:1) mixture gave 87.5 g of yellow crystals (yield 17.8% based on the amine).

| | Elementary analysis: | |
|---|---|---|
| | Calcd. for $C_{29}H_{25}N_3O$ (%) | Found (%) |
| C | 80.74 | 80.77 |
| H | 5.80 | 5.78 |
| N | 9.74 | 9.72 |

SYNTHESIS EXAMPLE 3 (SYNTHESIS OF HYDRAZONE COMPOUND No. 17)

1,1-diphenylhydrazine, prepared in the same manner as Synthesis Example 1, was dissolved in a mixture of 1 l of ethanol and 50 ml of acetic acid. After addition of 185.8 g (1.14 mol) of 2-formylbenzothiazole, represented by the formula

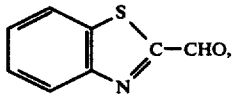

to this solution, condensation was carried out in the same manner as Synthesis Example 1. The resulting mixture was filtered and the filtrate was poured into water, thus giving a yellow precipitate. Recrystallization of the precipitate from methyl ethyl ketone gave 76.5 g of yellow crystals (yield 20.4% based on the amine).

| | Elementary analysis: | |
|---|---|---|
| | Calcd. for $C_{20}H_{15}N_3S$ (%) | Found (%) |
| C | 72.95 | 72.97 |
| H | 4.56 | 4.55 |
| N | 12.77 | 12.75 |

SYNTHESIS EXAMPLE 4 (SYNTHESIS OF HYDRAZONE COMPOUND NO. 21)

1,1-diphenylhydrazine, prepared in the same manner as Synthesis Example 1, was dissolved in a mixture of 1 l of ethanol and 50 ml of acetic acid. After addition of 167.6 g (1.14 mol) of 2-formylbenzoxazole, represented by the formula

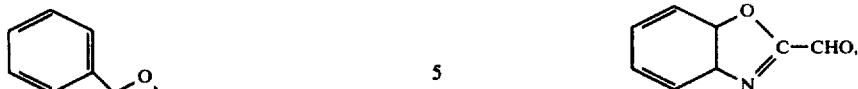

to this solution, condensation was carried out in the same manner as Synthesis Example 1. The resulting mixture was filtered and the filtrate was poured into water, thus giving a yellow precipitate. Recrystallization of the precipitate from methyl ethyl ketone gave 68 g of yellow crystals (yield 19.1% based on the amine).

| | Elementary analysis: | |
|---|---|---|
| | Calcd. for $C_{20}H_{15}N_3O$ (%) | Found (%) |
| C | 76.68 | 76.71 |
| H | 4.79 | 4.75 |
| N | 13.42 | 13.44 |

SYNTHESIS EXAMPLE 5 (SYNTHESIS OF HYDRAZONE COMPOUND NO. 27)

This hydrazone compound (81.2 g of yellow crystals) was obtained in the same manner as Synthesis Example 4 except for using 242.8 g (1.14 mol) of 2-formyl-β-naphthothiazole, represented by the formula

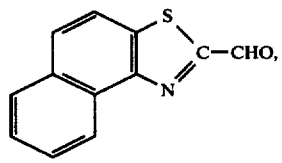

in place of 2-formylbenzoxazole (yield 18.8% based on the amine).

| | Elementary analysis: | |
|---|---|---|
| | Calcd. for $C_{24}H_{17}N_3S$ (%) | Found (%) |
| C | 75.99 | 76.01 |
| H | 4.49 | 4.46 |
| N | 11.08 | 11.10 |

SYNTHESIS EXAMPLE 6 (SYNTHESIS OF HYDRAZONE COMPOUND NO. 31)

This hydrazone compound (67.4 g of yellow crystals) was obtained in the same manner as Synthesis Example 4 except for using 198.4 g (1.14 mol) of 2-formyl-5-phenyl-1,3,4-oxadiazole, represented by the formula

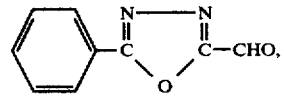

in place of 2-formylbenzoxazole (yield 17.2% based on the amine).

| | Elementary analysis: | |
|---|---|---|
| | Calcd. for $C_{21}H_{16}N_4O$ (%) | Found (%) |
| C | 74.12 | 74.14 |
| H | 4.71 | 4.70 |

-continued

| Elementary analysis: | |
|---|---|
| Calcd. for $C_{21}H_{16}N_4O$ (%) | Found (%) |
| N 16.47 | 16.44 |

SYNTHESIS EXAMPLE 7 (SYNTHESIS OF HYDRAZONE COMPOUND NO. 60)

1-phenyl-1-α-naphthylhydrazine, prepared in the same manner as Synthesis Example 1 except for using 250 g (1.14 mol) of N-α-naphthylaniline in place of diphenylamine, was dissolved in a mixture of 1 l of ethanol and 50 ml of acetic acid. After addition of 185.8 g (1.14 mol) of 2-formylbenzothiazole to this solution, condensation was carried out in the same manner as Synthesis Example 1. The resulting mixture was filtered and the filtrate was poured into water, thus giving a yellow precipitate. The precipitate was recrystallized three times from methyl ethyl ketone and 84.3 g of yellow crystals were obtained (yield 19.5% based on the amine).

| Elementary analysis: | |
|---|---|
| Calcd. for $C_{24}H_{17}N_3S$ (%) | Found (%) |
| C 75.99 | 75.96 |
| H 4.49 | 4.51 |
| N 11.08 | 11.06 |

SYNTHESIS EXAMPLE 8 (SYNTHESIS OF HYDRAZONE COMPOUND NO. 64)

This hydrazone compound (67 g of yellow crystals) was obtained in the same manner as Synthesis Example 7 except for using 167.6 g (1.14 mol) of 2-formylbenzoxazole in place of 2-formylbenzothiazole (yield 16.2% based on the amine).

| Elementary analysis: | |
|---|---|
| Calcd. for $C_{24}H_{17}N_3O$ (%) | Found (%) |
| C 79.34 | 79.36 |
| H 4.68 | 4.65 |
| N 11.57 | 11.59 |

SYNTHESIS EXAMPLE 9 (SYNTHESIS OF HYDRAZONE COMPOUND NO. 93)

1,1-diphenylhydrazine, prepared in the same manner as Synthesis Example 1, was dissolved in a mixture of 1 l of ethanol and 50 ml of acetic acid. After addition of 271.3 g (1.14 mol) of 3-acetyl-9-ethylcarbazole, represented by the formula

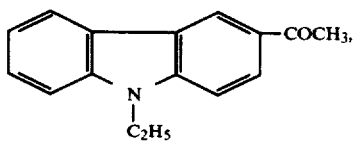

to this solution, condensation was carried out in the same manner as Synthesis Example 1. The resulting mixture was filtered and filtrate was poured into water, thus giving a yellow precipitate. The precipitate was recrystallized three times from methyl ethyl ketone and 97.4 g of yellow crystals were obtained (yield 21.2% based on the amine).

| Elementary analysis: | |
|---|---|
| Calcd. for $C_{28}H_{25}N_3$ (%) | Found (%) |
| C 83.37 | 83.38 |
| H 6.20 | 6.17 |
| N 10.43 | 10.45 |

SYNTHESIS EXAMPLE 10 (SYNTHESIS OF HYDRAZONE COMPOUND NO. 94)

1-benzyl-1-phenylhydrazine, prepared in the same manner as Synthesis Example 2, was condensed with 340.9 g (1.14 mol) of 3-benzoyl-9-ethylcarbazole, represented by the formula

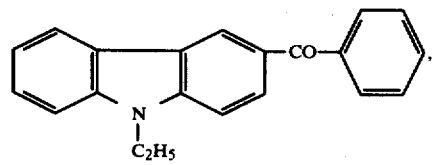

in the same manner as Synthesis Example 9, thus giving a yellow precipitate. This precipitate was recrystallized three times from methyl ethyl ketone and 94.4 g of yellow crystals were obtained (yield 17.8% based on the amine).

| Elementary analysis: | |
|---|---|
| Calcd. for $C_{33}H_{27}N_3$ (%) | Found (%) |
| C 85.16 | 85.15 |
| H 5.81 | 5.84 |
| N 9.03 | 9.01 |

The present hydrazone compounds can act effectively as a photoconductive material. They completely or almost completely transmit light irradiated to the charge generation layer mentioned later because of being sensitive to a light of relatively shorter wave length, and have an action to effectively transport carriers generated by light irradiation to the charge generation layer. Accordingly, the present hydrazone compounds are especially suited for use in photosensitive members which have the laminate structure comprising a charge generation layer and a charge transport layer.

In preferred embodiments of this invention, the charge transport layer can be formed by coating a solution of said hydrazone compound and a binder in a suitable solvent and drying the coating. Examples of said binder are acrylic resins, methacrylic resins, vinyl chloride resin, vinyl acetate resin, phenolic resins, epoxy resins, polyester resins, alkyd resins, polycarbonate resin, polyurethane resins, and copolymers containing two or more kinds of repeating units of these resins, of which particularly preferred are polyester resins and polycarbonate resin.

The mixing ratio of charge transporting material to binder is preferably 10–500:100 by weight. The thickness of charge transport layer is 2–100μ, preferably 5–30μ.

A variety of additives can be incorporated into the charge transport layer of this invention, including diphenyl, chlorinated diphenyl, o-terphenyl, p-terphenyl, dibutyl phthalate, dimethylglycol phthalate, dioctyl phthalate, triphenyl phosphate, methylnaphthalene, benzophenone, chlorinated paraffin, dilauryl thiopropionate, 3,5-dinitrosalicyclic acid, and various kinds of fluoro carbons.

The solvents to be used in formation of the charge transport layer of this invention include a number of conventionally useful organic solvents, of which typical ones are, for example, aromatic hydrocarbons and chlorinated aromatic hydrocarbons such as benzene, toluene, xylene, mesitylene, chlorobenzene, and the like; ketones such as acetone, 2-butanone, and the like; halogenated aliphatic hydrocarbons such as chloromethylene, chloroform, chloroethylene, and the like, cyclic or linear ethers such as tetrahydrofuran, ethyl ether, and the like, and mixtures thereof.

The charge generation layer used in this invention is the vacuum deposition layer or resin dispersed layer of a charge-generating material selected from selenium, selenium-tellurium, pyrylium dyes, thiopyrylium dyes, phthalocyanine pigments, anthoanthrone dyes, dibenzpyrenequinone pigments, pyranethrone pigments, trisazo pigments, disazo pigments, monoazo pigments, indigo pigments, quinacridone pigments, asymmetric quinocyanine dyes, quinocyanine-perylene dyes, and amorphous silicon (Japanese Patent Application Laid-Open No. 143645/1979).

The binders applicable for the charge generation layer include poly(vinyl butyral), poly(methyl methacrylate), polyesters, poly(vinylidene chloride), chlorinated rubbers, polyvinyltoluene, styrene-maleic anhydride copolymer, polystyrene, poly(vinyl chloride), ethylcellulose, polyamides, and styrene-butadiene copolymer.

The following monoazo, disazo, and trisazo pigments can be cited as specific examples of the charge-generating materials: disazo pigments having a biphenyl skeleton disclosed in Japanese Pat. Appln. Laid-Open Nos. 70538/ 1973, 4241/1977, 119926/1979, and 119927/1979; disazo pigments having a stilben skeleton disclosed in Japanese Pat. Appln. Laid-Open Nos. 8832/1977 and 20737/1979; disazo pigments having a styrylstilben skeleton disclosed in U.S. Pat. Nos. 4,256,821 and 4,272,598; disazo pigments having a distilben skeleton disclosed in U.S. Pat. No. 4,260,672; trisazo pigments having a triphenylamine skeleton disclosed in U.S. Pat. No. 4,279,981; disazo pigments having a carbazole skeleton disclosed in U.S. Pat. No. 4,251,614; disazo pigments having a distyrylcarbazole skeleton disclosed in Japanese Pat. Appln. Laid-Open No. 17734/1979; disazo pigments having a dibenzothiophene skeleton disclosed in Japanese Pat. Appln. Laid-Open No. 21728/1979; disazo pigments having a fluoroenone skeleton disclosed in Japanese Pat. Appln. Laid-Open No. 22834/1979; disazo pigments having a 2,5-diphenyloxadiazole skeleton disclosed in Japanese Pat. Appln. Laid-Opens Nos. 12742/1979 and 145142/1979; disazo pigments having a dibenzothiophene-5,5-dioxide skeleton disclosed in Japanese Pat. Appln. Laid-Open No. 20736/1979; disazo pigments having the coupler residue of a naphthalimide skeleton, disclosed in Japanese Pat. Appln. Laid-Open Nos. 79632/1979 and 117151/1980; and monoazo pigments having the coupler residue of a naphthalimide skeleton, disclosed in Japanese Pat. Appln. Laid-Open No. 17735/1979.

More specifically, the following azo pigments can be cited:

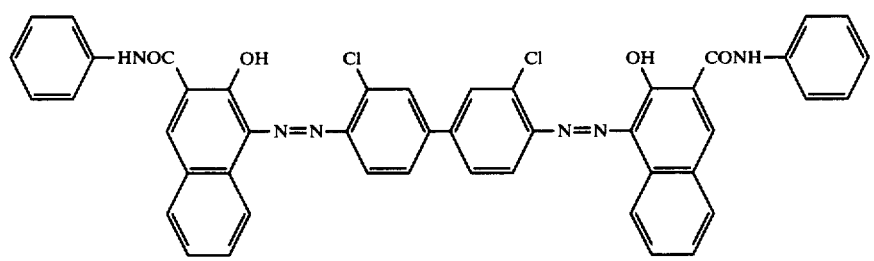

(1)

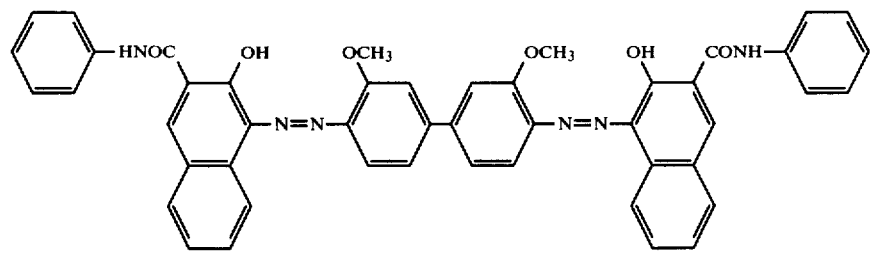

(2)

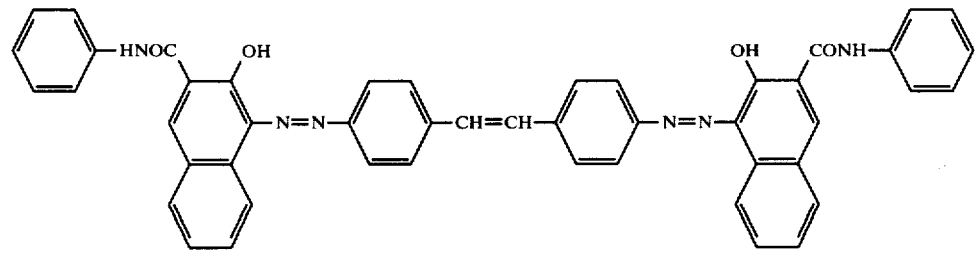

(3)

-continued
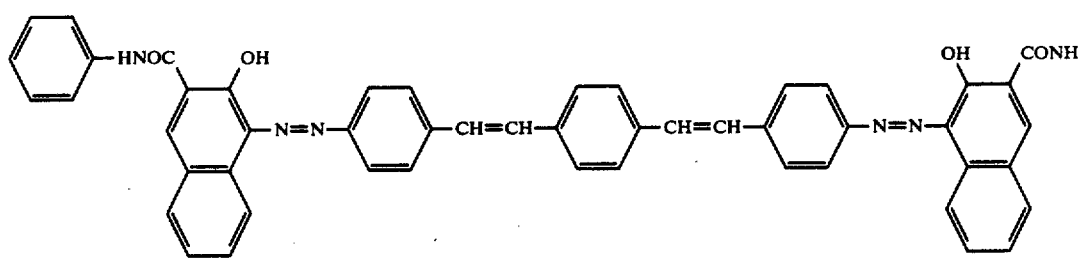
(4)
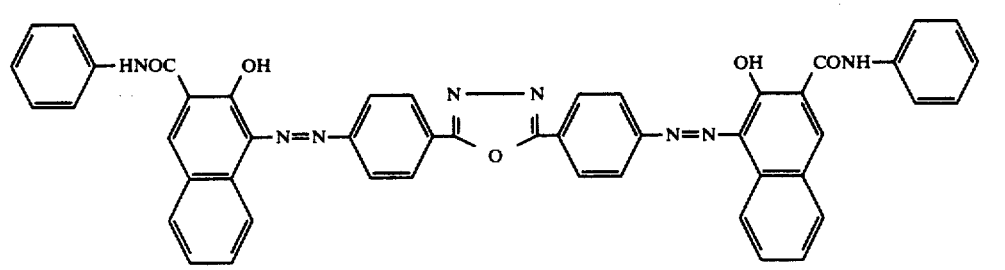
(5)
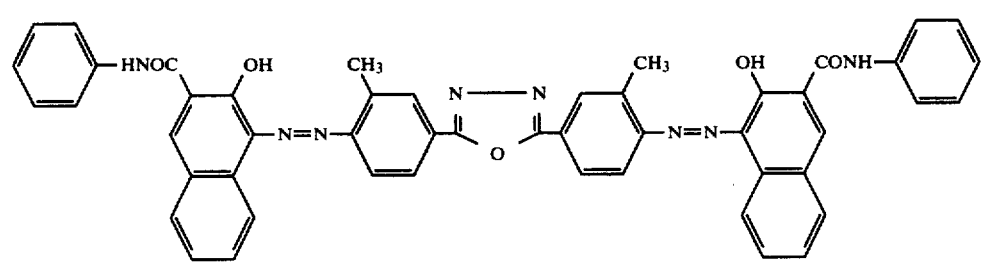
(6)
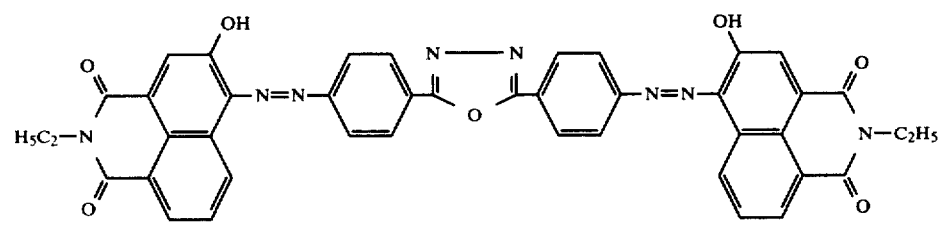
(7)
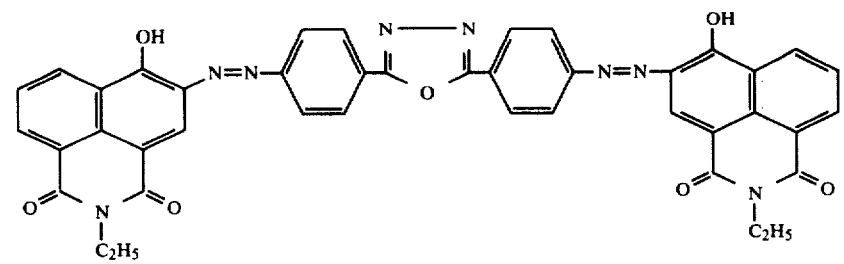
(8)
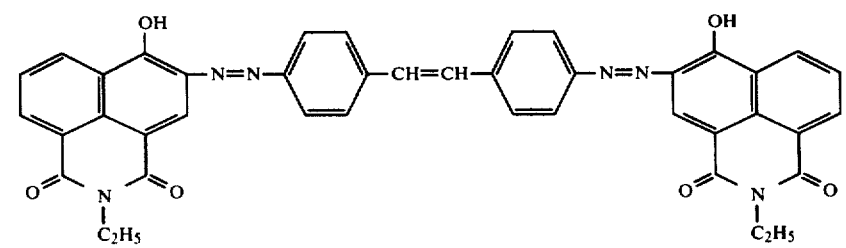
(9)

-continued
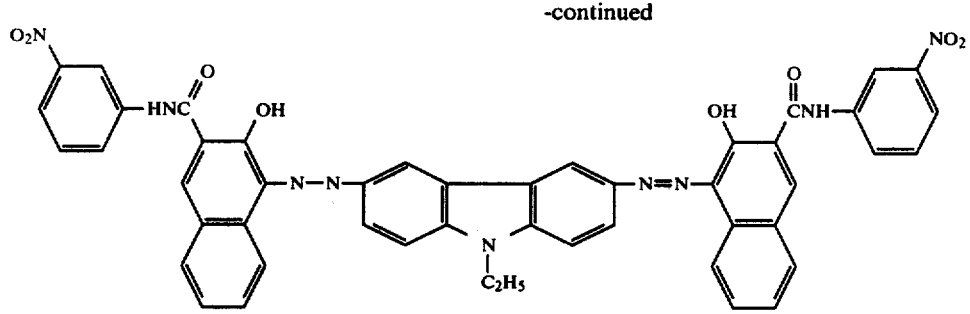
(10)
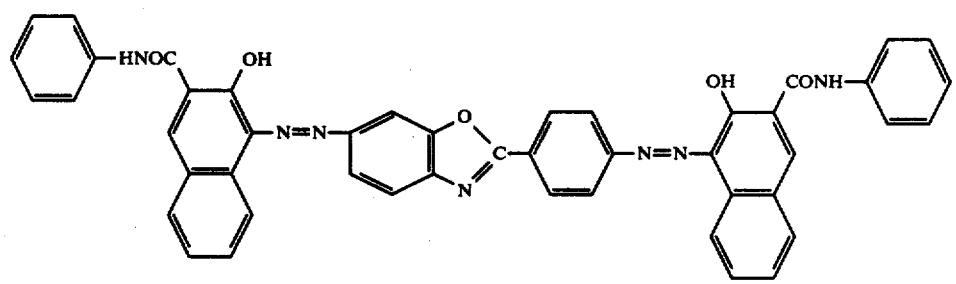
(11)
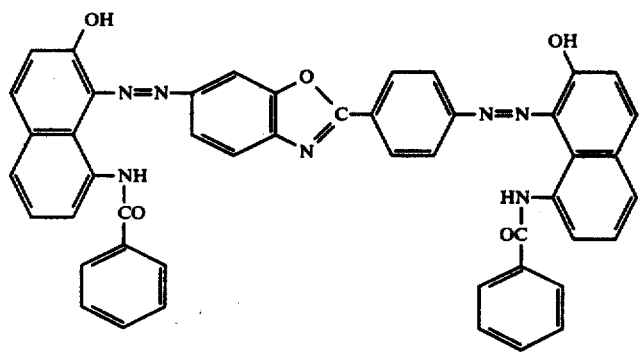
(12)
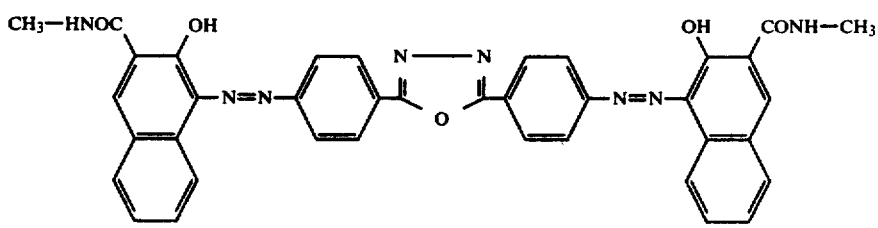
(13)
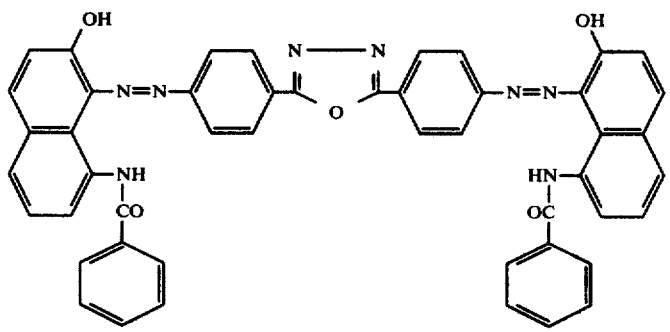
(14)
The following polycyclic quinone pigments can also be cited which have been disclosed in U.S. Pat. No. 3,877,935, and Japanese Pat. Appln. Laid-Open Nos. 17105/1980 and 98754/1980:

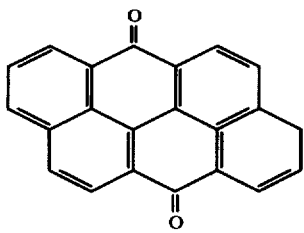

(15)

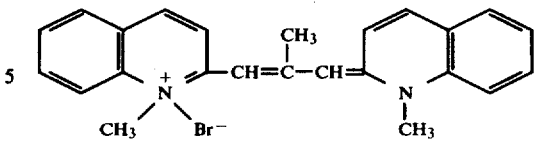

(21)

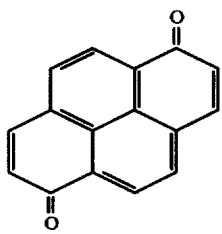

(16)

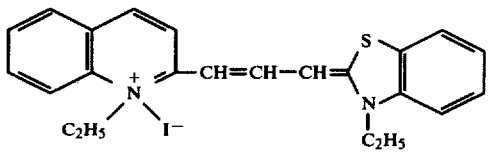

(22)

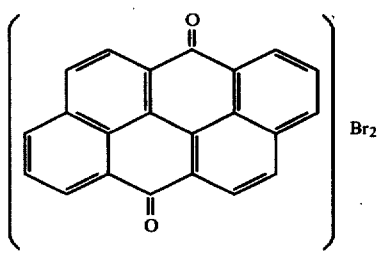

(17)

Further, there may be cited phthalocyanine pigments disclosed in Japanese Pat. Appln. Laid-Open Nos. 30329/1972, 11136/1974, 95852/1976, 108847/1976, 109841/1976, 117637/1976, and 129234/1976, e.g., copper phthalocyanines (x-, α-, β-, and ε-types) and derivatives thereof; perylene pigments such as

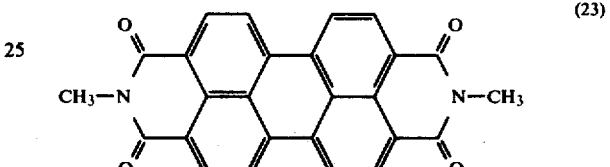

(23)

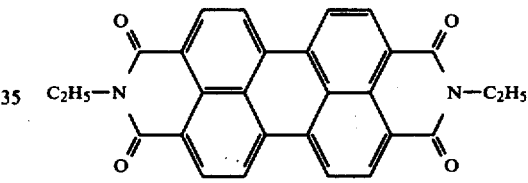

(18)

(19)

indigo dyes, and thioindigo dyes, disclosed in Japanese Pat. Appln. Laid-Open No. 48334/1974; methine dyes derived from squaric acid disclosed in U.S. Pat. No. 3,824,099; and an amorphous silicon layer and a vacuum deposited selenium-tellurium layer, disclosed in U.S. Pat. No. 4,265,991 and U.K. Laid-Open No. 2018446.

The charge generation layer may be formed in contact with the conductive support mentioned below, or formed on the charge transport layer.

The thickness of said charge generation layer is 0.005–20μ, preferably 0.05–10μ.

The electrophorographic photosensitive member of this invention may also have an intermediary layer upon a conductive supporting substrate, and upon said intermediary layer a charge generation layer and successively a charge transport layer may be formed. The intermediary layer is provided with the functions to bar the injection of free charges from the conductive substrate into the photosensitive layers of laminate structure when the photosensitive layers are charged and to bind or hold the photosensitive layers with the conductive substrate en masse. The materials applicable as the intermediary layer include aluminum oxide, indium oxide, tin oxide, an indium oxide-tin oxide mixture, polyethylene, polypropylene, acrylic resins, methacrylic resins, vinyl chloride resin, vinyl acetate resin, phenolic resins, epoxy resins, polyester resins, alkyd resins, polycarbonate resin, polyurethane resins, polyimide resins, vinylidene chloride resin, vinyl chlo- The following cyanine dyes can also cited which have been disclosed in Japanese Pat. Appln. Laid-Open Nos. 41230/1978, 42830/1978, 121739/1979, 121740/1979, 121741/1979, and 121742/1979:

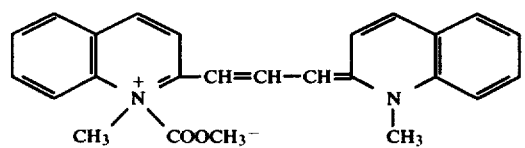

(20)

ride—vinyl acetate copolymer, polyamide resins, hydroxypropylcellulose, casein and poly(vinyl alcohol). The thickness of the intermediary or bond layer is 0.1–5μ, preferably 0.3–3μ. In a photosensitive member of laminate structure provided with a charge generation layer over a charge transport layer, such a metal oxide layer or polymer layer can also be formed as a protective layer for the charge generation layer.

The supporting substrates usable in the electrophotographic member of this invention include, for example, sheets of metals such as aluminum, vanadium, molybdenum, chromium, cadmium, titanium, nickel, copper, zinc, palladium, indium, tin, platinum, gold, stainless steel, and brass; and plastic sheets vacuum deposited or laminated with such metals. Shapes of the substrates, being not limited to a sheet form, may also be a cylinder form.

The hydrazone compounds used in this invention are hole-transporting, and hence when using a photosensitive member prepared by lamination in the order of conductive layer, charge generation layer, and charge transport layer containing the hydrazone compound, it is necessary to charge the surface of charge transport layer negatively. Upon charging and exposing the photosensitive member, holes generated in the charge generation layer in exposed areas are injected into the charge transport layer and then arrive at the surface and neutralize negative charges to decay the surface potential, thus resulting in an electrostatic contrast between exposed and non-exposed areas. For visualizing the electrostatic contrast, various conventional development processes can be applied.

The hydrazone compound of this invention can be used, besides as a charge-transporting material in the abovesaid laminate type of electrophotographic photosensitive member, for example, together with a co-crystalline complex of pyrylium dye and polycarbonate resin or a charge-transfer complex of poly(N-vinylcarbazole) and trinitrofluorenone to form a photosensitive layer.

The electrophotographic photosensitive member of this invention can be utilized not only in electrophotographic copying machines but also in a wide field of applications such as those to laser printers, CRT printers, and electrophotographic printing plate making systems.

This invention provides electrophotographic photosensitive members having a markedly improved sensitivity as compared with conventional ones, showing sufficiently repressed variations in light and dark portion potentials even when charge and exposure are repeated 10,000 times or more, and in addition having a good photomemory property.

This invention will be illustrated with reference to the following examples:

EXAMPLE 1

A β-type of copper phthalocyanine (trade name: Lionol Blue NCB Toner, produced by Toyo Ink Mfg. Co., Ltd.) was purified by heating under reflux successively in water, ethanol, and benzene and followed by filtration. Then, a coating liquid was prepared by mixing together 7 g of the purified pigment, 14 g of a polyester solution (trade name: Polyester Adhesive 49,000, 20% solids, manufactured by Du Pont de Nemours & Company), 35 g of toluene, and 35 g of dioxane, and dispersing the pigment by means of a ball mill. The coating liquid was applied on an aluminum sheet by use of a Meyer bar to form a charge generation layer of 0.5μ in dry thickness.

A coating solution was prepared by dissolving 7 g of the above-cited compound No. 1, thiazoline-2-carbaldhyde-N,N-diphenylhydrazone, as a charge-transporting material and 7 g of a polycarbonate resin (trade name: Panlite K-1300, manufactured by Teijin Kasei K. K.) with stirring in a mixed solvent consisting of 35 g of tetrahydrofuran and 35 g of chlorobenzene. The coating solution was applied on the charge generation layer to form a charge transport layer of 11μ in dry thickness. Thus, an electrophotographic member (sample 1) having a two-ply photosensitive layer was prepared.

Sample 1 was attached to the cylinder of an electrophotographic copying machine (Canon NP 5500 of Canon Co. was modified) to conduct sensitivity and durability tests. This copying machine provided with a negative-working corona charging unit, optical exposure system, development unit, transfer charging unit, discharge optical exposure system, and cleaner in that order around the cylinder, is designed to give images on sheets of transfer paper as the cylinder is driven. Samples set in the copying machine were adjusted to have a dark portion potential of ⊖500 V and a light portion potential of ⊖10 V by controlling the corona charging unit and the exposure quantity.

The sensitivity was evaluated by measuring the exposure quantity E½ (lux.sec) for halving the residual potential $V_S$ (volt) remaining after 5 sec. standing of corona charged sample in the dark. The durability was evaluated by measuring the values of light portion potential $V_L$ (volt) and of dark portion potential $V_D$ (volt) at the 1st, 5000th, 10,000th, and 25,000th image formations. The results of sample 1 are shown in Table 1.

TABLE 1

| Sample No. | E1/2 | Durability test | | | | | | | |
|---|---|---|---|---|---|---|---|---|---|
| | | 1st | | 5,000th | | 10,000th | | 25,000th | |
| 1 | 18.0 | $V_D$ −500 | $V_L$ −10 | $V_D$ −530 | $V_L$ −20 | $V_D$ −480 | $V_L$ −20 | $V_D$ −470 | $V_L$ −30 |

The photomemory property was evaluated by measuring the time required for the sample exposed to light at an intensity of 600 lux for 3 minutes, to recover in the dark the original charge bearing characteristics. The recovery time of sample 1 was 2 minutes. The shorter the recovery time is, the better photomemory property.

EXAMPLES 2–21

Electrophotographic photosensitive members (samples 2–21) were prepared in the same manners as Example 1 except for using the above-cited hydrazone compounds Nos. (2), (5), (6), (7), (12), (13), (16), (17), (18), (21), (22), (24), (25), (27), (28), (31), (33), (35), (38) and (42) respectively as charge-transporting compounds in place of the above-cited hydrazone compound No. (1).

The results of sensitivity, durability, and photomemory tests are shown in Table 2, but in these examples the corona charging was effected evenly at ⊖5 KV with omitting control of the quantity of charge given to sample.

TABLE 2

| Sample No. | Charge-transporting Compound | | $E1/2$ | Durability Test | | | | | | | | Photomemory test (min.) |
|---|---|---|---|---|---|---|---|---|---|---|---|---|
| | | | | 1st | | 5,000th | | 10,000th | | 25,000th | | |
| | | | | $V_D$ | $V_L$ | $V_D$ | $V_L$ | $V_D$ | $V_L$ | $V_D$ | $V_L$ | |
| 2 | Hydrazone Compound | (2) | 16.5 | −500 | −20 | −500 | −10 | −480 | −20 | −480 | −25 | 2 |
| 3 | Hydrazone Compound | (5) | 19.2 | −520 | −10 | −520 | −20 | −500 | −20 | −490 | −25 | 6 |
| 4 | Hydrazone Compound | (6) | 4.5 | −480 | −10 | −460 | −10 | −460 | −20 | −450 | −40 | 5 |
| 5 | Hydrazone Compound | (7) | 10.0 | −490 | −10 | −490 | −10 | −450 | −20 | −460 | −20 | 8 |
| 6 | Hydrazone Compound | (12) | 3.2 | −450 | −10 | −450 | −10 | −420 | −20 | −430 | −40 | 3 |
| 7 | Hydrazone Compound | (13) | 15.7 | −530 | −15 | −520 | −20 | −520 | −25 | −520 | −30 | 4 |
| 8 | Hydrazone Compound | (16) | 7.5 | −500 | −10 | −490 | −10 | −490 | −20 | −480 | −25 | 10 |
| 9 | Hydrazone Compound | (17) | 14.0 | −550 | −20 | −550 | −20 | −520 | −10 | −520 | −30 | 2 |
| 10 | Hydrazone Compound | (18) | 2.9 | −450 | −10 | −430 | −10 | −420 | −20 | −420 | −40 | 2 |
| 11 | Hydrazone Compound | (21) | 14.5 | −520 | −10 | −520 | −20 | −520 | −30 | −500 | −40 | 6 |
| 12 | Hydrazone Compound | (22) | 4.2 | −440 | −10 | −440 | −10 | −450 | −10 | −430 | −40 | 9 |
| 13 | Hydrazone Compound | (24) | 8.0 | −490 | −10 | −490 | −20 | −470 | −10 | −470 | −20 | 12 |
| 14 | Hydrazone Compound | (25) | 3.5 | −430 | −10 | −420 | −20 | −410 | −15 | −420 | −40 | 10 |
| 15 | Hydrazone Compound | (27) | 11.5 | −520 | −10 | −520 | −10 | −500 | −30 | −490 | −20 | 7 |
| 16 | Hydrazone Compound | (28) | 12.0 | −550 | −30 | −550 | −20 | −520 | −20 | −510 | −25 | 5 |
| 17 | Hydrazone Compound | (31) | 14.2 | −490 | −10 | −480 | −20 | −470 | −30 | −460 | −30 | 12 |
| 18 | Hydrazone Compound | (33) | 10.5 | −450 | −10 | −450 | −20 | −440 | −20 | −420 | −30 | 11 |
| 19 | Hydrazone Compound | (35) | 9.5 | −510 | −20 | −500 | −10 | −500 | −20 | −480 | −30 | 16 |
| 20 | Hydrazone Compound | (38) | 7.8 | −420 | −10 | −420 | −20 | −410 | −20 | −400 | −30 | 7 |
| 21 | Hydrazone Compound | (42) | 6.5 | −440 | −10 | −440 | −10 | −410 | −20 | −400 | −50 | 10 |

COMPARATIVE EXAMPLES 1-9

Electrophotographic photosensitive members (comparative samples 1-9) were prepared in the same manner as Example 1 except for using the compounds shown in Table 3, respectively as charge-transporting compounds in place of the above-cited hydrazone compound No. (1).

TABLE 3

| Comparative Sample No. | Charge-transporting compound for comparison |
|---|---|
| 1 | 1,1-bis(4-N,N—dibenzylamino-2-methylphenyl)propane |
| 2 | 2,5-bis(4-N,N—diethylaminophenyl)-1,3,4-oxadiazole |
| 3 | poly(N—vinylcarbazole) |
| 4 | 1,1-bis(4-N,N—diethylamino-2-methylphenyl)heptane |
| 5 | 1-phenyl-3-(4-N,N—diethylaminostyryl)-5-(4-N,N—diethylaminophenyl)pyrazoline |
| 6 | 4-N,N—diethylaminobenzaldehyde-N,N—diphenylhydrazone |
| 7 | N—ethylcarbazole-3-carbaldehyde-N,N—diphenylhydrazone |
| 8 | pyridine-2-carbaldehyde-N,N—diphenylhydrazone |
| | furan-2-carbaldehyde-N,N—diphenylhydrazone |

These comparative samples were tested for sensitivity, durability, and photomemory in the same way as Example 2.

The results are shown in Table 4.

TABLE 4

| Comparative Sample No. | $E\frac{1}{2}$ | Durability Test | | | | | | | | Photomemory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 1 | 28.0 | −650 | −150 | −600 | −200 | −510 | −200 | −500 | −250 | 40 |
| 2 | 12.5 | −420 | −100 | −420 | −150 | −420 | −200 | −380 | −200 | 25 |
| 3 | 15.8 | −720 | −180 | −750 | −200 | −750 | −200 | −450 | −100 | 40 |
| 4 | 35.5 | −670 | −200 | −550 | −200 | −500 | −260 | −450 | −280 | 40 |
| 5 | 9.5 | −450 | −10 | −400 | −60 | −400 | −70 | −370 | −90 | 30 |
| 6 | 4.2 | −390 | −10 | −300 | −20 | −280 | −30 | −250 | −40 | 40 |
| 7 | 7.5 | −500 | −10 | −500 | −50 | −450 | −50 | −400 | −60 | 40 |
| 8 | 8.9 | −360 | −10 | −330 | −20 | −330 | −50 | −300 | −80 | 30 |

TABLE 4-continued

| Comparative Sample No. | E½ | Durability Test | | | | | | | | Photo-memory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 9 | 6.5 | −550 | −200 | −550 | −200 | −560 | −250 | −570 | −250 | 40 |

As can be seen from Tables 1, 2 and 4, electrophotographic photosensitive members of this invention (samples 1–21) have higher sensitivity, exhibit less variations in light and dark portion potentials when a great number of repetition of charge and exposure are made, and are better in photomemory property, as compared with comparative samples 1–9.

EXAMPLE 22

A charge generation layer was formed using an apparatus, as shown in FIG. 1, set up in a perfectly shielded clean room, in the following way.

A surface-cleaned molybdenum plate 101 (substrate) of 0.2 mm in thickness and 5 cm in diameter was securely fastened to a fixing member 102 provided at a prescribed position in a glow discharge vacuum deposition chamber 109. The substrate 101 was heated by a heater 103 incorporated in the fixing member 102 with a precision of ±0.5° C. A thermocouple (chromel-alumel couple) had been fitted therein to measure directly the temperature of the substrate rear surface. After confirmation that all valves in the system are closed, a main valve 104 was fully opened to evacuate the chamber 109 to about $5 \times 10^{-6}$ Torr. Then, the input voltage to the heater 103 was raised and controlled to settle the temperature of the substrate to a constant value of 150° C., while detecting said temperature.

Then, an auxiliary valve 105 and subsequently outflow valves 106, 107 and 108 were fully opened to evacuate flow meters 110, 111 and 112 sufficiently to a high degree of vacuum. After closure of valves 106, 107 and 108, the valve 114 of bomb 113 containing a silane gas (99.999% purity) was opened, the pressure of a bomb outlet pressure gauge 115 was adjusted to 1 kg/cm², and an inflow valve 116 was gradually opened to introduce silane gas into the flow meter 110. Successively, the outflow valve 106 and then the auxiliary valve 105 were gradually opened and the latter valve opening was controlled while watching the reading of a Pirani gauge 117, to adjust the pressure of chamber 109 to $1 \times 10^{-2}$ Torr. After the chamber pressure had settled, the opening of the main valve 104 was gradually closed until the reading of Pirani gauge came to 0.5 Torr. After confirmation of the inner pressure stabilization, a high-frequency power source 118 was switched on to apply 5 MHz high-frequency power to an induction coil 119, thereby generating a glow discharge in the inner space surrounded by the coil of chamber 109 (the upper portion of the chamber), where input power was 30 W. Under these conditions amorphous silicon film was developed on the substrate. After maintenance of the same conditions for 1 hour, the high-frequency power source 118 was switched off to intermit the glow discharge. In this state, the valve of the bomb 120 containing a diborane gas (99.999% purity) was opened, the pressure of an outlet pressure gauge 121 was adjusted, an inflow valve 122 was gradually opened to introduce the diborane gas into a flow meter 111, then the outflow valve 107 was gradually opened, and its opening was controlled to settle the flow of diborane gas to 0.08% of the silane gas flow, while reading the flow meter 111.

The high-frequency power source 118 was then switched on to recommence glow discharge. The glow discharge was continued for one hour, and then the heater 103 and the high-frequency power source 118 were switched off. After the substrate was cooled down to 100° C., the outflow valves 106 and 107 were closed and the main valve 104 was fully opened to evacuate the chamber to $10^{-5}$ Torr or less. Then, the main valve 104 was closed and a leak valve 123 was opened to return the chamber to atmospheric pressure, and the substrate was taken out. In this case, the total thickness of amorphous silicon base layer formed on the substrate was about 3μ. Subsequently, the same charge transport layer as of sample 1 of Example 1 was formed on the amorphous silicon base layer thus prepared.

The sensitivity, durability, and photomemory test results on the photosensitive member (sample 22) thus prepared are shown in Table 5.

TABLE 5

| Sample No. | E½ | Durability Test | | | | | | | | Photo-memory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 22 | 10.3 | −500 | −10 | −520 | −20 | −500 | −30 | −470 | −30 | 3 |

EXAMPLE 23

A dispersion liquid was prepared by mixing 5 g of a purified Diane Blue (C.I. 21180) and 2 g of a poly(vinyl butyral) resin (trade name: Eslex BM-2, manufactured by Sekisui Chemical Co., LTD.) with 50 g of ethanol, and grinding the mixture in a ball mill for 30 hours. The dispersion liquid was coated on an aluminum substrate to form a charge generation layer of 0.2μ in dry thickness.

Then, the same charge transport layer as of sample 1 of Example 1 was formed on the charge generation layer thus prepared.

The photosensitive member (sample 23) thus prepared was tested for sensitivity, durability, and photomemory in the same way as Example 2. The results are shown in Table 6.

COMPARATIVE EXAMPLE 10

An electrophotographic photosensitive member for comparison (comparative sample 10) was prepared in the same manner as Example 23 except for using 2,5-bis(4-N,N-diethylaminophenyl)-1,3,4-oxadiazole as a charge-transporting compound in place of the above-cited hydrazone compound No. (1).

The sample thus prepared was tested for sensitivity, durability, and photomemory in the same way as Example 2. The results are shown also in Table 6.

ple 1 except for using the above-cited hydrazone compound Nos. (45), (48), (49), (50), (55), (56), (59), (60), (61), (64), (65), (67), (68), (70), (71), (74), (76), (80), (83)

TABLE 6

| Sample No. | $E_{\frac{1}{2}}$ | Durability Test | | | | | | | | Photomemory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 23 | 12.0 | −520 | −20 | −550 | −20 | −490 | −10 | −480 | −30 | 3 |
| Comparative sample 10 | 15.0 | −410 | −80 | −410 | −100 | −390 | −120 | −360 | −150 | 30 |

As is evident also from Examples 22 and 23 and Comparative Example 10, electrophotographic photosensitive members of this invention have much improved in sensitivity, characteristics in repeated operations, and photomemory property.

and (87) as charge-transporting compounds, respectively, in place of the above-cited hydrazone compound No. (1).

These samples were tested for sensitivity, durability and photomemory in the same way as Example 2. The results are shown in Table 8.

TABLE 8

| Sample No. | Charge-transporting Compound | $E_{\frac{1}{2}}$ | Durability Test | | | | | | | | Photomemory Test (min.) |
|---|---|---|---|---|---|---|---|---|---|---|---|
| | | | 1st | | 5,000th | | 10,000th | | 25,000th | | |
| | | | $V_D$ | $V_L$ | $V_D$ | $V_L$ | $V_D$ | $V_L$ | $V_D$ | $V_L$ | |
| 25 | Hydrazone Compound (45) | 14.0 | −500 | −20 | −500 | −10 | −480 | −20 | −480 | −30 | 2 |
| 26 | Hydrazone Compound (48) | 15.7 | −510 | −10 | −520 | −20 | −500 | −20 | −490 | −25 | 5 |
| 27 | Hydrazone Compound (49) | 3.2 | −480 | −10 | −470 | −20 | −460 | −30 | −460 | −40 | 8 |
| 28 | Hydrazone Compound (50) | 8.0 | −490 | −10 | −490 | −10 | −480 | −10 | −480 | −45 | 10 |
| 29 | Hydrazone Compound (55) | 3.0 | −490 | −10 | −480 | −20 | −470 | −20 | −470 | −20 | 2 |
| 30 | Hydrazone Compound (56) | 13.5 | −550 | −15 | −540 | −15 | −540 | −15 | −500 | −25 | 4 |
| 31 | Hydrazone Compound (59) | 3.5 | −520 | −10 | −510 | −20 | −510 | −20 | −500 | −20 | 9 |
| 32 | Hydrazone Compound (60) | 12.0 | −570 | −15 | −560 | −15 | −560 | −20 | −550 | −30 | 2 |
| 33 | Hydrazone Compound (61) | 2.5 | −480 | −10 | −480 | −20 | −470 | −10 | −470 | −40 | 2 |
| 34 | Hydrazone Compound (64) | 12.5 | −520 | −10 | −510 | −15 | −510 | −25 | −500 | −30 | 5 |
| 35 | Hydrazone Compound (65) | 4.0 | −440 | −10 | −440 | −20 | −430 | −40 | −430 | −45 | 3 |
| 36 | Hydrazone Compound (67) | 4.2 | −490 | −10 | −490 | −30 | −480 | −20 | −480 | −25 | 7 |
| 37 | Hydrazone Compound (68) | 2.8 | −460 | −10 | −450 | −30 | −450 | −30 | −440 | −40 | 11 |
| 38 | Hydrazone Compound (70) | 10.5 | −530 | −10 | −520 | −10 | −510 | −20 | −490 | −30 | 2 |
| 39 | Hydrazone Compound (71) | 10.5 | −540 | −15 | −540 | −15 | −530 | −20 | −530 | −30 | 6 |
| 40 | Hydrazone Compound (74) | 5.0 | −550 | −15 | −540 | −15 | −540 | −35 | −530 | −40 | 12 |
| 41 | Hydrazone Compound (76) | 5.5 | −480 | −10 | −470 | −20 | −450 | −35 | −450 | −40 | 13 |
| 42 | Hydrazone Compound (80) | 8.5 | −520 | −20 | −500 | −20 | −500 | −30 | −480 | −30 | 11 |
| 43 | Hydrazone Compound (83) | 7.2 | −430 | −10 | −430 | −20 | −420 | −30 | −410 | −30 | 3 |
| 44 | Hydrazone Compound (87) | 5.0 | −470 | −10 | −450 | −10 | −430 | −30 | −420 | −40 | 5 |

EXAMPLE 24

A photosensitive member (sample 24) was prepared in the same manner as Example 1 except for using the above-cited hydrazone compound No. (44) in place of the above-cited hydrazone compound No. (1). The sensitivity, durability, and photomemory test results on this sample are shown in Table 7.

EXAMPLE 45

A charge generation layer based on amorphous silicon was formed in the same manner as Example 22, and then the same charge transport layer as of Example 24 was formed on the amorphous silicon base layer. The photosensitive member (sample 45) thus prepared was

TABLE 7

| Sample No. | $E_{\frac{1}{2}}$ | Durability Test | | | | | | | | Photomemory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 24 | 15.0 | −500 | −10 | −520 | −20 | −480 | −20 | −480 | −30 | 2 |

EXAMPLES 25–44

Electrophotographic photosensitive members (samples 25–44) were prepared in the same manner as Example 1 except for using the above-cited hydrazone comtested for sensitivity, durability, and photomemory in the same way as Example 2. The results are shown in Table 9.

TABLE 9

| Sample No. | E½ | Durability Test | | | | | | | | Photo-memory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 45 | 5.5 | −520 | −5 | −510 | −15 | −500 | −15 | −490 | −20 | 3 |

EXAMPLE 46

A charge generation layer containing Diane Blue was formed in the same manner as Example 23, and the same charge transport layer as of Example 24 was formed on the charge generation layer. The photosensitive member (sample 46) thus prepared was tested for sensitivity, durability and photomemory in the same way as Example 2. The results shown in Table 10.

TABLE 10

| Sample No. | E½ | Durability Test | | | | | | | | Photo-memory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 46 | 10.0 | −540 | −10 | −540 | −10 | −530 | −20 | −530 | −30 | 4 |

EXAMPLE 47

A photosensitive member (sample 47) was prepared in the same manner as Example 1 except for using the above-cited hydrazone compound No. (89) as a charge-transporting compound in place of the above-cited hydrazone compound No. (1). The sensitivity, durability, and photomemory test results on this sample are shown in Table 11.

TABLE 11

| Sample No. | E½ | Durability Test | | | | | | | | Photo-memory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 47 | 5.2 | −510 | −10 | −500 | −15 | −500 | −20 | −470 | −30 | 3 |

EXAMPLES 48–56

Photosensitive members (samples 48–56) were prepared in the same manner as Example 1 except for using the above-cited hydrazone compound Nos. (90), (91), (92), (93), (94), (95), (96) and (97) as charge-transporting compounds, respectively, in place of the above-cited hydrazone compound No. (1). These samples were tested for sensitivity, durability, and photomemory in the same way as Example 2. The results are shown in Table 12.

TABLE 12

| Sample No. | Charge-transporting Compound | E½ | Durability Test | | | | | | | | Photomemory Test (min.) |
|---|---|---|---|---|---|---|---|---|---|---|---|
| | | | 1st | | 5,000th | | 10,000th | | 25,000th | | |
| | | | $V_D$ | $D_L$ | $V_D$ | $V_L$ | $V_D$ | $V_L$ | $V_D$ | $V_L$ | |
| 48 | Hydrazone Compound (90) | 6.2 | −520 | −5 | −500 | −10 | −470 | −20 | −450 | −30 | 5 |
| 49 | Hydrazone Compound (91) | 4.8 | −510 | −5 | −500 | −10 | −480 | −20 | −470 | −30 | 2 |
| 50 | Hydrazone Compound (92) | 7.3 | −550 | −10 | −530 | −15 | −500 | −15 | −480 | −30 | 8 |
| 51 | Hydrazone Compound (93) | 7.5 | −560 | −10 | −540 | −10 | −500 | −30 | −490 | −30 | 8 |
| 52 | Hydrazone Compound (94) | 8.2 | −550 | −15 | −520 | −20 | −500 | −30 | −470 | −35 | 6 |
| 53 | Hydrazone Compound (95) | 6.1 | −510 | −10 | −480 | −20 | −480 | −20 | −460 | −30 | 7 |
| 54 | Hydrazone Compound (96) | 7.2 | −520 | −5 | −510 | −15 | −510 | −15 | −480 | −35 | 6 |
| 55 | Hydrazone Compound (97) | 8.1 | −550 | −5 | −510 | −15 | −480 | −20 | −450 | −30 | 5 |
| 56 | Hydrazone Compound (98) | 6.7 | −500 | −5 | −470 | −10 | −470 | −20 | −450 | −35 | 7 |

EXAMPLE 57

A solution of casein in aqueous ammonia (casein 11.2 g, 28% aqueous ammonia 1 g, water 222 ml) was coated by means of a Meyer bar on an aluminum plate to form a bond layer (intermediary layer) of 1.0 g/m² after drying.

Then, a coating liquid prepared by dispersing 5 g of a disazo pigment having the structure

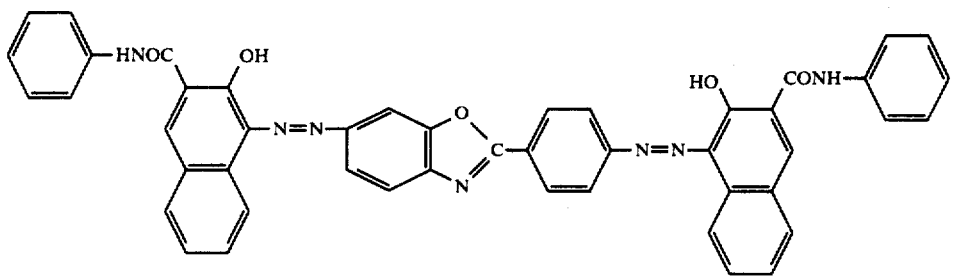

in a solution of 2 g of a poly(vinyl butyral) resin (degree of butyral conversion: 63 mol%) in 95 ml of ethanol was applied on the bond layer to form a charge generation layer of 0.2 g/m² after drying.

Further, 5 g of the above-cited hydrazone compound No. (89) and 5 g of a polycarbonate resin (bisphenol A based polycarbonate, viscosity average molecular weight: 30,000) were dissolved in 150 ml of dichloromethane, and the resulting solution was coated on the charge generation layer to form a charge transport layer of 10 g/m² after drying.

The photosensitive member (sample 57) thus prepared was corona-charged at ⊖5 KV in the electrostatic process by using an electrostatic copying paper testing machine (Model SP-428, manufactured by Kawaguchi Denki K. K.), retained for 10 seconds in a dark, and then exposed to light at an intensity of 5 lux, to examine charge bearing characteristics. The results are shown in Table 13, wherein $V_O$ is original potential (volt), $R_V$ is potential retention (%) after standing for 10 seconds in a dark, and $E_{\frac{1}{2}}$ is exposure quantity (lux.sec) for halving original potential.

TABLE 13

| Sample No. | Charge-transporting compound | $V_O$ | $R_V$ | $E_{\frac{1}{2}}$ |
|---|---|---|---|---|
| 57 | Hydrazone compound No. (1) | −530 | 94 | 4.8 |

EXAMPLE 58

A charge generation layer based on amorphous silicon was prepared in the same manner as Example 22, and the same charge transport layer as of Example 47 was formed on the amorphous silicon base layer. The photosensitive member (sample 58) thus prepared was tested for sensitivity, durability, and photomemory in the same way as Example 2. The results are shown in Table 14.

TABLE 14

| Sample No. | $E_{\frac{1}{2}}$ | Durability Test | | | | | | | | Photo-memory Test (min.) |
|---|---|---|---|---|---|---|---|---|---|---|
| | | 1st | | 5000th | | 10000th | | 25000th | | |
| | | $V_D$ | $V_L$ | $V_D$ | $V_L$ | $V_D$ | $V_L$ | $V_D$ | $V_L$ | |
| 58 | 4.9 | −480 | −10 | −460 | −10 | −460 | −15 | −450 | −20 | 3 |

EXAMPLE 59

A pigment having the structure

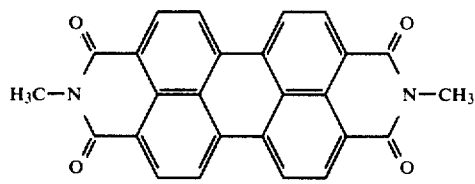

was vacuum-deposited on an aluminum plate of 100μ in thickness to form a charge generation layer of 0.15μ thickness.

Then, a solution prepared by dissolving 5 g of the above-cited hydrazone compound No. (89) and 5 g of a polyester resin (Vylon 200, manufactured by Toyobo Co., Ltd.) in 150 ml of dichloromethane was coated on the charge generation layer to form charge transport layer of 11 g/m² after drying.

The photosensitive member thus prepared was tested for charge bearing characteristics in the same way as Example 57. The results are shown in Table 15.

TABLE 15

| | |
|---|---|
| $V_O$ | −530 V |
| $R_V$ | 92% |
| $E_{\frac{1}{2}}$ | 5.8 lux. sec |

EXAMPLE 60

An aqueous solution of hydroxypropylcellulose was coated on an aluminum plate to form a bond layer of 0.6 g/m² after drying.

After 5 g of the above-cited hydrazone compound No. (90), 5 g of poly(N-vinylcarbazole), and 0.1 g of 2,4,7-trinitrofluorenone were dissolved in 150 ml of dichloromethane, 1.0 g of the same disazo pigment as used in Example 57 was added thereto and dispersed, and the resulting dispersion was coated on the bond layer to form a photosensitive layer of 11 g/m² after drying.

The photosensitive member (sample 60) thus prepared was tested for charge bearing characteristics in the same way as Example 57. The results are shown in Table 16.

TABLE 16

| | |
|---|---|
| $V_O$ | 430 V |
| $R_V$ | 90% |
| $E_{\frac{1}{2}}$ | 14.2 lux. sec |

What we claim is:

1. An electrophotographic photosensitive member comprisng a layer containing a hydrazone compound represented by the following formula (1) or (2):

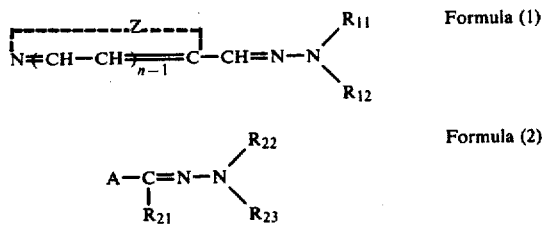

wherein, Z is an atomic group necessary to complete a substituted or unsubstituted heterocyclic ring; selected from the group consisting of thiazoline, oxazoline, imidazoline, thiazole, oxazole, imidazole, benzothiazole, benzoxazole, benzimidazole, naphthothiazole, naphthoxazole, naphthoimidazole, quinoline, isoquinoline, quinoxaline, pyridazine, pyrimidine, pyrazine, triazole, oxadiazole, and thiadiazole; $R_{21}$, $R_{22}$ and $R_{23}$ represent substituted or unsubstituted alkyl, substituted or unsubstituted aralkyl, or substituted or unsubstituted aryl, and the combinations of $R_{11}$ with $R_{12}$ and of $R_{22}$ with $R_{23}$ can form each a pyrrolidine ring, piperidine ring, or morpholine ring; n is 1 or 2, and A is a monovalent heterocyclic ring residue.

2. An electrophotographic photosensitive member of claim 1, wherein said hydrazone compound is represented by formula (1) of which Z, when n is 1, is an atomic group necessary to complete a substituted or unsubstituted heterocyclic ring of thiazoline, oxazoline, imidazoline, thiazole, oxazole, imidazole, benzothiazole, benzoxazole, benzimidazole, naphthothiazole, naphthoxazole, naphthimidazole, 2-quinoline, isoquinoline, quinoxaline, pyridazine, pyrimidine, pyrazine, triazole, oxadiazole, or thiadiazole.

3. An electrophotographic photosensitive member of claim 2, wherein said hydrazone compound is represented by formula (1) of which Z, when n is 1, is an atomic group necessary to complete a substituted or unsubstituted heterocyclic ring of thiazole, benzothiazole, naphthothiazole, oxazole, benzoxazole, or naphthoxazole.

4. An electrophotographic photosensitive member of claim 3, wherein said hydrazone compound is represented by formula (1) of which Z, when n is 1, is an atomic group necessary to complete a substituted or unsubstituted heterocyclic ring of thiazole or benzothiazole.

5. An electrophotographic photosensitive member of claim 1, wherein said hydrazone compound is represented by formula (1) where at least one of $R_{11}$ and $R_{12}$ is phenyl, toryl, alkoxyphenyl, α-naphthyl, or β-naphthyl.

6. An electrophotographic photosensitive member of claim 5, wherein said hydrazone compound is represented by formula (1) where $R_{12}$ is methyl, ethyl, 2-hydroxyethyl, phenyl, tolyl, alkoxyphenyl, benzyl, α-naphthyl, or β-naphthyl.

7. An electrophotographic photosensitive member of claim 1, wherein said hydrazone compound is represented by formula (2) of which A is a monovalent residue of substituted or unsubstituted heterocyclic ring of pyrrole, pyrazole, pyrimidine, pyridazine, pyridine, indole, benzimidazole, carbazole, furan, oxazole, benzoxazole, benzofuran, dibenzofuran, thiophene, thiazole, or benzothiazole.

8. An electrophotographic photosensitive member of claim 7, wherein said hydrazone compound is represented by formula (2) of which A is a monovalent residue of substituted or unsubstituted heterocyclic ring of carbazole, thiazole, or benzothiazole.

9. An electrophotographic photosensitive member of claim 1, wherein said hydrazone compond is represented by formula (2) wherein $R_{21}$ is methyl, ethyl, propyl, phenyl, dialkylaminophenyl or benzyl.

10. An electrophotographic photosensitive member of claim 1, wherein said hydrazone compound is represented by formula (2) where at least one of $R_{22}$ and $R_{23}$ is phenyl, tolyl, alkoxyphenyl, α-naphthyl, or β-naphthyl.

11. An electrophotographic photosensitive member of claim 10, wherein said hydrazone compound is represented by formula (2) where $R_{23}$ is methyl, ethyl, 2-hydroxyethyl, phenyl, tolyl, alkoxyphenyl, benzyl, α-naphthyl or β-naphthyl.

12. An electrophotographic photosensitive member of claim 1, wherein a layer containing said hydrazone compound is a charge transport layer.

13. An electrophotographic photosensitive member of claim 12, wherein a charge generation layer is provided contiguously to said charge transport layer.

14. An electrophotographic photosensitive member of claim 13, wherein said charge transport layer is laid on the charge generation layer.

15. An electrophotographic photosensitive member of claim 14, wherein said charge generation layer is laid on a conductive layer.

16. An electrophotographic photosensitive member of claim 15, wherein an intermediary layer is provided between said charge generation and conductive layers.

17. An electrophotographic photosensitive member of claim 12, wherein said charge transport layer contains at least one selected from acrylic resins, methacrylic resins, vinyl chloride resin, vinyl acetate resin, phenolic resins, epoxy resins, polyester resins, alkyd resins, polycarbonate resin, and polyurethane resins.

18. An electrophotographic photosensitive member of claim 17, wherein said charge transport layer has a thickness of 2–100μ.

19. An electrophotographic photosensitive member of claim 18, wherein said charge transport layer has a thickness of 5–30μ.

20. An electrophotographic photosensitive member of claim 13, wherein said charge generation layer contains at least one of selenium, selenium-tellurium, pyrylium dyes, thiopyrylium dyes, phthalocyanine pigments, anthoanthrone pigments, dibenzopyrene quinone pigments, pyranthrone pigments, trisazo pigments, disazo pigments, monoazo pigments, indigo pigments, quinacridone pigments, asymmetric quinocyanine dyes, quinocyanine dyes, perylene pigments, and amorphous silicon.

21. An electrophotographic photosensitive member of claim 20, wherein said charge generation layer comprises a vacuum deposit layer of selenium, selenium-tellurium, or a perylene pigment.

22. An electrophotographic photosensitive member of claim 20, wherein said charge generation layer comprises a trisazo or disazo pigment and a binder.

23. An electrophotographic photosensitive member of claim 22, wherein said binder is at least one of poly(vinyl butyral), poly(methyl methacrylate), polystyrene, poly(vinylidene chloride), chlorinated rubber, polyvinyltoluene, styrene-maleic anhydride copolymer, polyesters, poly(vinyl chloride), ethylcellulose, polyamides and styrene-butadiene copolymer.

24. An electrophotographic photosensitive member of claim 23, wherein said binder is poly(vinyl butyral).

25. An electrophotographic photosensitive member of claim 20, wherein said charge generation layer comprises amorphous silicon layer prepared by glow discharge.

26. An electrophotographic photosensitive member of claim 13, wherein said charge generation layer has a thickness of 0.005–20μ.

27. An electrophotographic photosensitive member of claim 26, wherein said charge generation layer has a thickness of 0.05–10μ.

* * * * *